United States Patent
Freeman et al.

(10) Patent No.: US 9,066,902 B2
(45) Date of Patent: Jun. 30, 2015

(54) FATTY ACIDS AS ANTI-INFLAMMATORY AGENTS

(75) Inventors: Bruce A. Freeman, Pittsburgh, PA (US); Francisco J. Schopfer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 106 days.

(21) Appl. No.: 13/387,489

(22) PCT Filed: Aug. 2, 2010

(86) PCT No.: PCT/US2010/002141
§ 371 (c)(1),
(2), (4) Date: Feb. 8, 2012

(87) PCT Pub. No.: WO2011/014261
PCT Pub. Date: Feb. 3, 2011

(65) Prior Publication Data
US 2012/0136034 A1  May 31, 2012

Related U.S. Application Data

(60) Provisional application No. 61/213,946, filed on Jul. 31, 2009.

(51) Int. Cl.
| A61K 31/33 | (2006.01) |
| C07D 487/00 | (2006.01) |
| A61K 31/12 | (2006.01) |
| A61K 31/231 | (2006.01) |
| A61K 31/232 | (2006.01) |

(52) U.S. Cl.
CPC ............... *A61K 31/12* (2013.01); *A61K 31/231* (2013.01); *A61K 31/232* (2013.01)

(58) Field of Classification Search
None
See application file for complete search history.

(56) References Cited

U.S. PATENT DOCUMENTS 7,776,916 B2 *  8/2010  Freeman et al. ............. 514/558
2004/0176451 A1  9/2004  Tamai et al.

FOREIGN PATENT DOCUMENTS

| EP | 1 407 767 | 4/2004 |
| WO | WO 02/102364 | 12/2002 |
| WO | WO-2005/073164 A1 | 8/2005 |
| WO | WO 2006/055965 | 5/2006 |
| WO | WO-2008/011085 A1 | 1/2008 |
| WO | WO 2008/103753 | 8/2008 |

OTHER PUBLICATIONS

Clapp et al. Biochemistry 2006(45) 15884-15892.*
Hung The Dang et al. J. Nat. Prod. 2008 (71) 232-240.*
Cheol Min Kim et al. J. Med. Chem. 2001 (44) 2479-2485.*
Alois Furstner et al. Chem Asian J. 2008 (3) 310-318.*
Bindi Dangi et al., "Biogenic Synthesis, Purification, and Chemical Characterization of Anti-inflammatory Resolvins Derived from Docosapentaenoic Acid (DPAn-6)", The Journal of Biological Chemistry, vol. 284, No. 22, May 29, 2009, pp. 14744-14759.
International Search Report PCT/US2010/002141 dated Nov. 24, 2010.
Toshimasa Itoh et al., "Synthesis of docosahexaenoic acid derivatives designed as novel PPARγ agonists and antidiabetic agents", Bioorganic and Medicinal Chemistry 14(2006) 98-108.
Groeger et al., "Discovery, Structural Characterization and Quantification of Novel Inflammatory-Induced Electrophilic Fatty Acid Derivatives," *Free Radical Biology & Medicine*, 45(1): S134 (2008).
Groeger et al., "Cyclooxygenase-2 generates anti-inflammatory mediators from omega-3 fatty acids," Nature Chemical Biology, 6(6): 433-441 (Jun. 2010).
Serhan et al., "Anti-Inflammatory Actions of Neuroprotectin D1/Protectin D1 and Its Natural Stereoisomers: Assignments of Dihydroxy-Containing Docosatrienes" *The Journal of Immunology*, 176: 1848-1859, 2006.

* cited by examiner

*Primary Examiner* — Jeffrey S Lundgren
*Assistant Examiner* — Michael Schmitt
(74) *Attorney, Agent, or Firm* — Klarquist Sparkman, LLP

(57) ABSTRACT

Compounds of formula I and their metabolites are potent mediators of an inflammatory response: (I) where a, b, c, d, e, f, V, W, X, Y, $R^a$, $R^{a'}$, $R^b$, $R^{b'}$, $R^c$, and $R^{c'}$ are defined herein. In particular, the compounds of the invention are candidate therapeutics for treating inflammatory conditions.

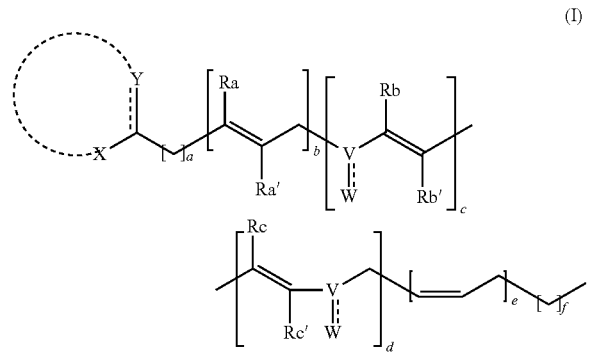

16 Claims, 27 Drawing Sheets

FATTY ACIDS AS ANTI-INFLAMMATORY AGENTS

CROSS-REFERENCE TO RELATED PATENT APPLICATIONS

This application claims priority to U.S. provisional application No. 61/213,946, filed Jul. 31, 2009, the entire contents of which are incorporated herein by reference.

STATEMENT REGARDING FEDERALLY SPONSORED RESEARCH

This invention was made with United States government support under grant numbers R01 HL58115 and R01 HL64937, awarded by the National Institutes of Health. The United States government has certain rights in the invention.

BACKGROUND OF THE INVENTION

Electrophilic fatty acids are important transducers of biochemical information. For example, nitro fatty acids mediate cell signaling activities that are anti-inflammatory in nature. See U.S. Patent Publication No. 20070232579. It is believed that these signaling events are regulated by a reversible and covalent modification of the sulfhydryl group of a protein by an electrophilic lipid which results in modifications of several downstream events such as protein phosphorylation and activation of transcription to name a few.

Similar to the nitro fatty acids, electrophilic keto fatty acids also regulate inflammatory response. The keto fatty acids are generated during inflammation due to the up regulation of the enzyme cyclooxygenase-2 (COX-2). COX is responsible for formation of important biological mediators called prostanoids (including prostaglandins, prostacyclin and thromboxane), of which the prostaglandins are important pro-inflammatory molecules. Groeger et al. disclose certain electrophilic fatty acids that are generated during inflammation and that the corresponding oxo-derivatives were generated by a COX-2 catalyzed mechanism in activated macrophages. See Groeger et al., Cyclooxygenase-2-generates anti-inflammatory mediators from omega-3 fatty acids, *Nature Chemical Biology* 6, 433-441 (2010).

Of the three known COX isoenzymes (COX-1, COX-2 and COX-3), prostaglandins produced by COX-2 are associated pain and inflammation. Thus, agents capable of inhibiting COX-2 have been used as therapeutics for treating pain and reducing inflammation.

While selective COX-2 inhibitors are currently known, these compounds display associated toxic side effects. Thus, their use as therapeutics in the treatment of chronic pain and inflammation has been limited.

SUMMARY OF THE INVENTION

The present invention provides, in one of its aspects a formulation comprising (A) a keto fatty acid according to Formula I, and (B) a pharmaceutically acceptable carrier.

In Formula (I), X is selected from the group consisting of —$CH_2$—, —OH, —S, —$OR^t$ and —$NR^pR^q$; Y is selected from the group consisting of —C(O)—, O, —S—, and —$NR^pR^q$; W is selected from the group consisting of —OH, —H, =S, —$SR^p$, —C(O)H, —C(O), —C(O)$R^p$, —COOH, —COO$R^p$, —Cl, —Br, —I, —F, —$CF_3$, —CN, —$SO_3$, —$SO_2R^p$, —$SO_3H$, —$NH_3^+$, —$NH_2R^{p+}$, —$NR^pR^qR^t$, $NO_2$, =O, =$NR^p$, =$CF_2$, and =CHF and V is —CH— when W is selected from the group consisting of —OH, —H, —C(O)H, —C(O), —C(O)$R^p$, —COOH, —COO$R^p$, —Cl, —Br, —I, —F, —$CF_3$, —CN, —$SO_3$, —$SO_2R^p$, —$SO_3H$, —$NH_3^+$, —$NH_2R^{p+}$, —$NR^pR^qR^t$ and $NO_2$ and V is —C— when W is selected from the group consisting of =O, =$NR^p$, =$CF_2$, and =CHF.

The indices a, b, c, d, e, and f independently are integers between 0 and 15 inclusive. In one embodiment c is 0 when d is not 0. Alternatively, d is 0 when c is not 0; such that the sums (a+b+c+e+f) and (a+b+d+e+f) independently are equal to an integer that conforms to the formula 2n or 2n+1, wherein n is an integer between 3 and 15 inclusive.

Substituents —$R^p$, —$R^q$ and —$R^t$ are independently selected from H, ($C_1$-$C_8$)alkyl and ($C_1$-$C_8$)haloalkyl. In Formula I —$R^a$, —$R^{a'}$, —$R^b$, —$R^{b'}$, —$R^c$, —$R^{c'}$, are independently selected from the group consisting of —H, —OH, —C(O)H, —C(O), —C(O)$R^p$, —COOH, —COO$R^p$, —Cl, —Br, —I, —F, —$CF_3$, —$CHF_2$, —$CH_2F$, —CN, —$SO_3$, —$SO_2R^p$, —$SO_3H$, —$NH_3^+$, —$NH_2R^{p+}$, —$NR^pR^qR^t$ and $NO_2$. Additionally, —$R^a$ and —$R^{a'}$ do not simultaneously represent non-hydrogen groups; —$R^b$ and —$R^{b'}$ do not simultaneously represent non-hydrogen groups; and, similarly, —$R^c$ and —$R^{c'}$ do not simultaneously represent non-hydrogen groups.

In Formula I, an optional double bond is indicated by ====, while

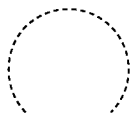

when present, together with X and Y and the carbon atom to which they are bonded represents a 5- to 6-membered heterocyclyl or heteroaryl ring. Compounds 13-oxo-(7Z,10Z,14A,16Z,19Z)-docosa-7,10,14,16,19-pentanoic acid, 17-oxo-(7Z,10Z,13Z,15A,19Z)-docosa-7,10,13,15,19-pentanoic acid, 13-OH (7Z,10Z,14A,16Z,19Z)-docosa-7,10,14,16;19-pentanoic acid, 17-OH (7Z,10Z,13Z,15A,19Z)-docosa-7,10,13,15,19-pentanoic acid, 13-oxo-(4Z,7Z,10Z,14A,16Z,19Z)-docosa-4,7,10,14,16,19-hexanoic acid, 17-oxo-(4Z,7Z,10Z,13Z,15A,19Z)-docosa-4,7,10,13,15,19-hexanoic acid, 13-OH-(4Z,7Z,10Z,14A,16Z,19Z)-docosa-4,7,10,14,16,19-hexanoic acid or 17-OH-(4Z,7Z,10Z,13Z,15A,19Z)-docosa-

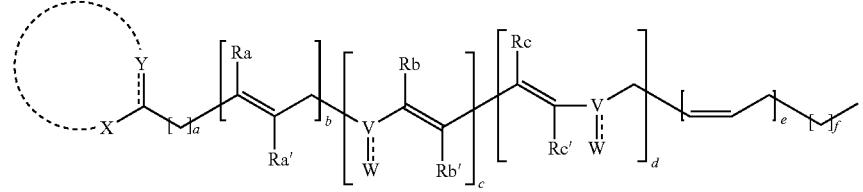

(I)

4,7,10,13,15,19-hexanoic acid where A indicates either E or Z configuration are not covered by Formula I.

In another embodiment, the pharmaceutical formulation comprises a fatty acid selected from the following list 13-oxo-(7Z,10Z,14A,16Z,19Z)-docosa-7,10,14,16,19-pentanoic acid, 17-oxo-(7Z,10Z,13Z,15A,19Z)-docosa-7,10,13,15,19-pentanoic acid, 13-oxo-(4Z,7Z,10Z,14A,16Z,19Z)-docosa-4,7,10,14,16,19-hexanoic acid, 17-oxo-(4Z,7Z,10Z,13Z,15A,19Z)-docosa-4,7,10,13,15,19-hexanoic acid, where A indicates either E or Z configuration and a pharmaceutically acceptable carrier.

The present invention also provides a method for treating a subject suffering from an inflammatory condition comprising administering to the subject a therapeutically effective amount of a fatty acid according to Formula (I). In another aspect, the invention provides a method for treating a subject suffering from an inflammatory condition by administrating a pharmaceutical formulation comprising a fatty acid selected from the group consisting of 13-oxo-(7Z,10Z,14A,16Z,19Z)-docosa-7,10,14,16,19-pentanoic acid, 17-oxo-(7Z,10Z,13Z,15A,19Z)-docosa-7,10,13,15,19-pentanoic acid, 13-OH (7Z,10Z,14A,16Z,19Z)-docosa-7,10,14,16,19-pentanoic acid, 17-OH (7Z,10Z,13Z,15A,19Z)-docosa-7,10,13,15,19-pentanoic acid, 13-oxo-(4Z,7Z,10Z,14A,16Z,19Z)-docosa-4,7,10,14,16,19-hexanoic acid, 17-oxo-(4Z,7Z,10Z,13Z,15A,19Z)-docosa-4,7,10,13,15,19-hexanoic acid, 13-OH-(4Z,7Z,10Z,14A,16Z,19Z)-docosa-4,7,10,14,16,19-hexanoic acid or 17-OH-(4Z,7Z,10Z,13Z,15A,19Z)-docosa-4,7,10,13,15,19-hexanoic acid where A indicates either E or Z configuration.

Exemplary inflammatory conditions that are treated using the inventive formulation are organ preservation for transplantation, osteoarthritis, chronic obstructive pulmonary disease (COPD), atherosclerosis, hypertension, allograft rejection pelvic inflammatory disease, ulcerative colitis, Crohn's disease, allergic inflammation in the lung, cachexia, stroke, congestive heart failure, pulmonary fibrosis, hepatitis, glioblastoma, Guillain-Barre Syndrome, systemic lupus erythematosus viral myocarditis, post-transplantation organ protection, acute pancreatitis, irritable bowel disease general inflammation, autoimmune disease, autoinflammatory disease, arterial stenosis, organ transplant rejection and burns, and chronic conditions such as, chronic lung injury and respiratory distress, insulin-dependent diabetes, non-insulin dependent diabetes, hypertension, obesity, arthritis, neurodegenerative disorders, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia areta, ischemia, myocardial infarction, arterial stenosis, rheumatoid arthritis, coronary restenosis, neurocognitive decline and insulin resistance.

In another embodiment the invention provides a method for detecting a metabolite of a fatty acid according to Formula (I). Detection of one or more fatty acid metabolites is accomplished by contacting with a biological sample at least one fatty acid according to formula I:

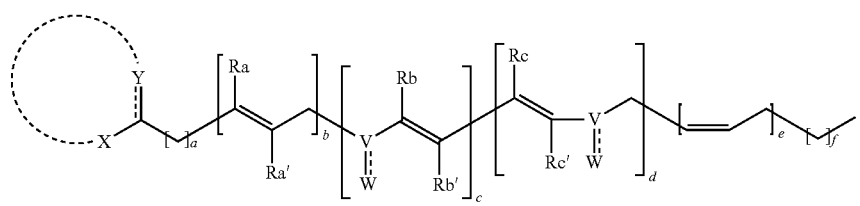

(I)

In Formula (I), X is selected from the group consisting of —$CH_2$—, —OH, —S, —$OR^t$ and —$NR^pR^q$, Y is selected from the group consisting of —C(O)—, O, —S—, and —$NR^pR^q$, W is selected from the group consisting of —OH, —H, =S, —$SR^p$—C(O)H, —C(O), —C(O)$R^p$, —COOH, —COO$R^p$, —Cl, —Br, —I, —F, —$CF_3$, —CN, —$SO_3$, —$SO_2R^p$, —$SO_3$H, —$NH_3^+$, —$NH_2R^{p+}$, —$NR^pR^qR^t$, $NO_2$, =O, =$NR^p$, =$CF_2$, and =CHF and V is —CH— when W is selected from the group consisting of —OH, —H, —C(O)H, —C(O), —C(O)$R^p$, —COOH, —COO$R^p$, —Cl, —Br, —I, —F, —$CF_3$, —CN, —$SO_3$, —$SO_2R^p$, —$SO_3$H, —$NH_3^+$, —$NH_2R^{p+}$, —$NR^pR^qR^t$ and $NO_2$ and V is —C— when W is selected from the group consisting of =O, =$NR^p$, =$CF_2$, and =CHF.

The indices a, b, c, d, e, and f independently are integers between 0 and 15 inclusive. In one embodiment c is 0 when d is not 0. Alternatively, d is 0 when c is not 0; such that the sums (a+b+c+e+f) and (a+b+d+e+f) independently are equal to an integer that conforms to the formula 2n or 2n+1, wherein n is an integer between 3 and 15 inclusive.

Substituents —$R^p$, —$R^q$ and —$R^t$ are independently selected from H, ($C_1$-$C_8$)alkyl and ($C_1$-$C_8$)haloalkyl. In Formula I —$R^a$, —$R^{a'}$, —$R^b$, —$R^{b'}$, —$R^c$, —$R^{c'}$, are independently selected from the group consisting of —H, —OH, —C(O)H, —C(O), —C(O)$R^p$, —COOH, —COO$R^p$, —Cl, —Br, —I, —F, —$CF_3$, —$CHF_2$, —$CH_2$F, —CN, —$SO_3$, —$SO_2R^p$, —$SO_3$H, —$NH_3^+$, —$NH_2R^{p+}$, —$NR^pR^qR^t$ and $NO_2$. Additionally, —$R^a$ and —$R^{a'}$ do not simultaneously represent non-hydrogen groups; —$R^b$ and —$R^{b'}$ do not simultaneously represent non-hydrogen groups; and, similarly, —$R^c$ and —$R^{c'}$ do not simultaneously represent non-hydrogen groups.

In Formula I, an optional double bond is indicated by ===, while

when present, together with X and Y and the carbon atom to which they are bonded represents a 5- to 6-membered heterocyclyl or heteroaryl ring.

According to the inventive method, a cellular lysate is optionally prepared depending on the nature of the biological sample. The biological sample or cellular lysate is then incubated with β-mercaptoethanol (BME), for a time sufficient to allow formation of a mixture containing one or more covalent BME-fatty acid adducts. The identification of one or more fatty acid metabolites is carried out by subjecting the cellular extract containing BME to mass spectrometry.

DETAILED DESCRIPTION OF THE PREFERRED EMBODIMENTS

Definitions

Figure 1:
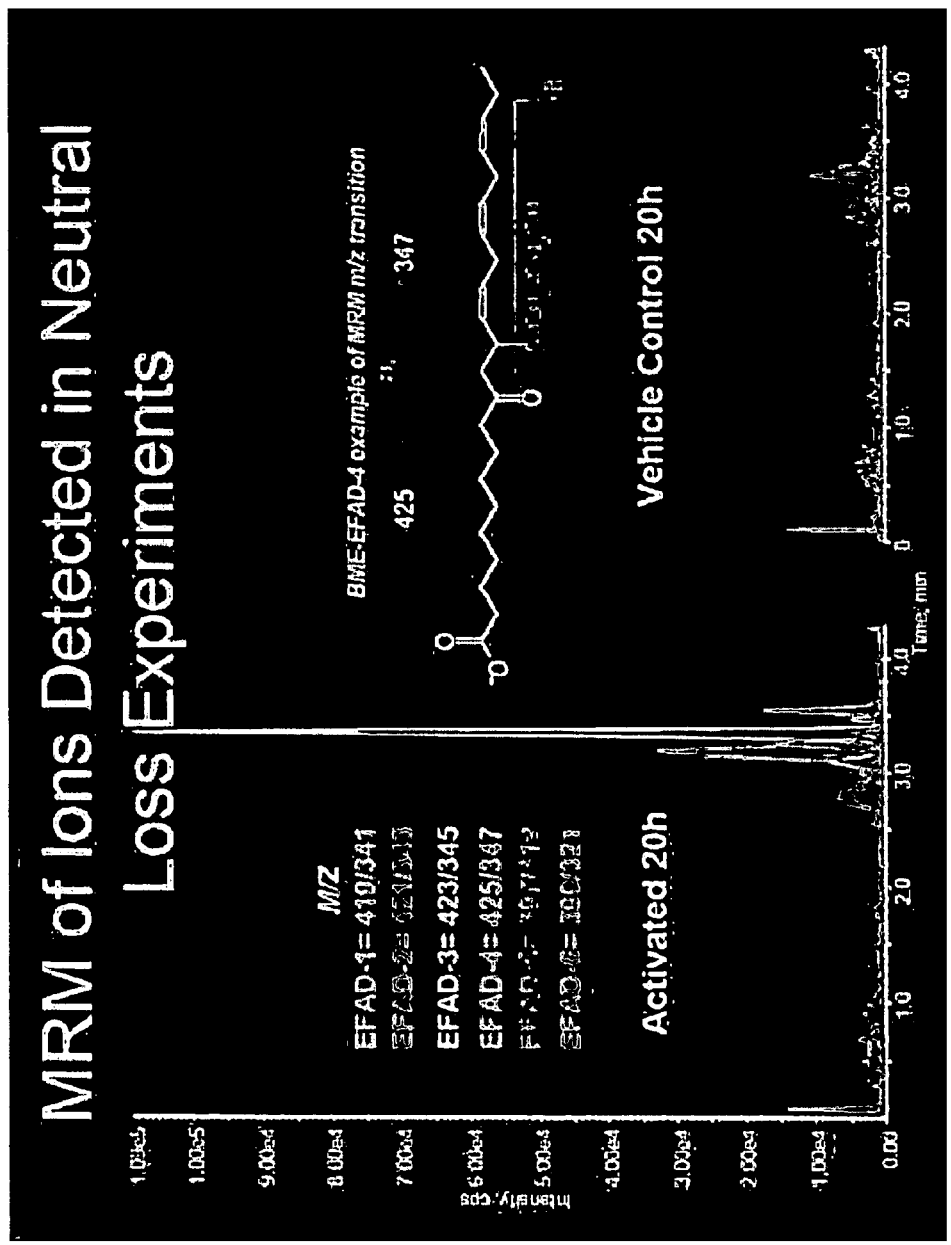
FIG. 1 is a representative mass spectrum for ions detected upon fragmentation of a BME-keto fatty acid adduct.
Figure 2:
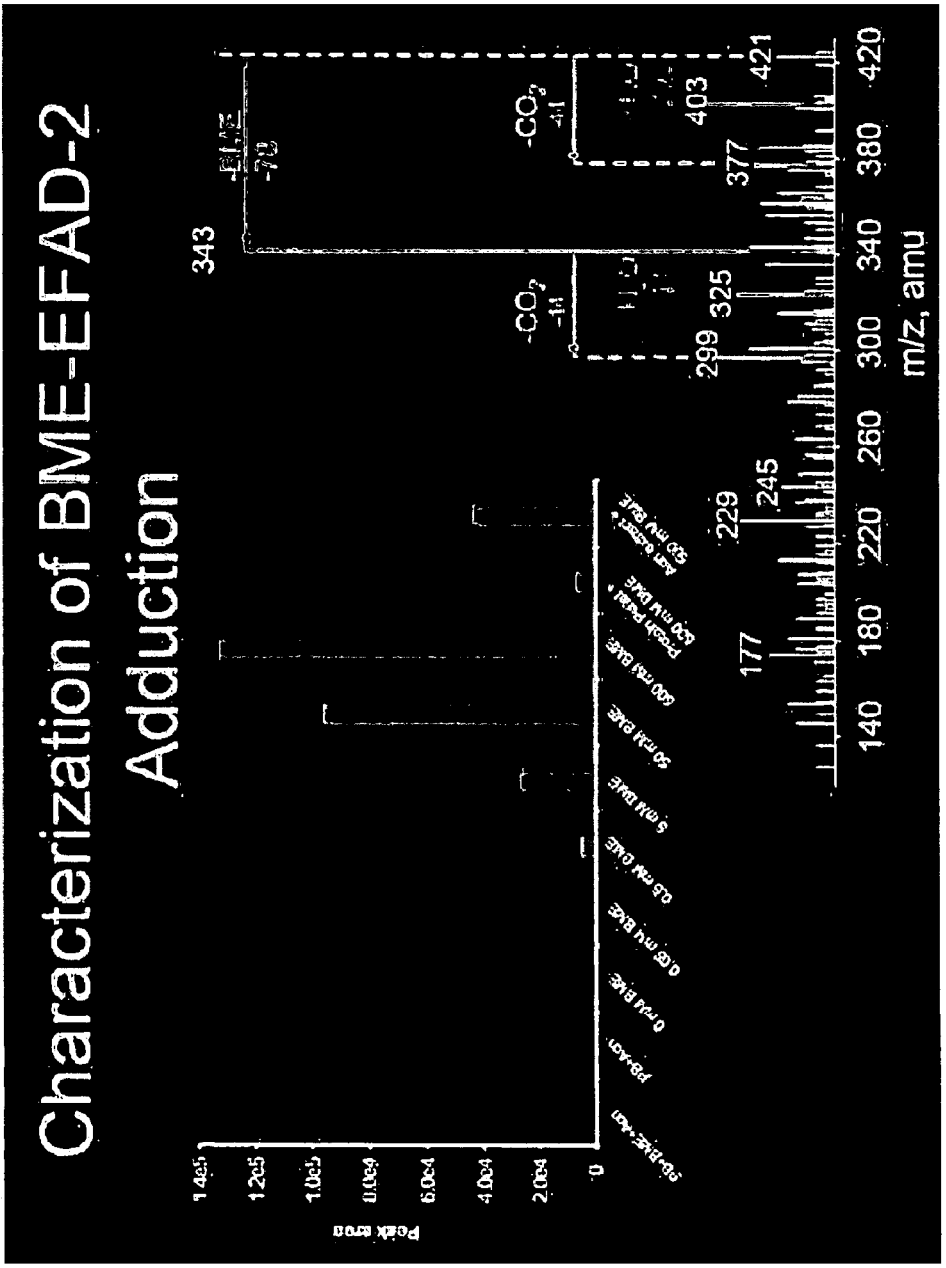
FIG. 2 shows the mass of representative ion peaks obtained by fragmentation of a BME-keto fatty acid adduct.

The term "alkyl" is used in this description to denote a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

An "alkenyl group" is as a branched or unbranched hydrocarbon group of 2 to 24 carbon atoms and structural formula containing at least one carbon-carbon double bond.

The phrase "alkynyl group" as employed here refers to a branched or unbranched hydrocarbon group of 2 to 24 carbon atoms and containing at least one carbon-carbon triple bond.

As used herein, "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include but are not limited to phenyl, naphthyl, tetrahydronaphthyl, chlorophenyl, methylphenyl, methoxyphenyl, trifluoromethylphenyl, nitrophenyl, and 2,4-methoxychlorophenyl.

The term "halogen" and "halo" refers to —F, —Cl, —Br or —I.

The term "heteroatom" is meant to include oxygen (O), nitrogen (N), and sulfur (S).

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "haloalkoyl," refers to an —($C_1$-$C_8$)alkyl group wherein one or more hydrogen atoms in the $C_1$-$C_8$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "amine or amino" refers to an —$NR^pR^q$ group wherein $R^p$ and $R^q$ each independently refer to a hydrogen, ($C_1$-$C_8$)alkyl, ($C_1$-$C_8$)haloalkyl, and ($C_1$-$C_6$)hydroxyalkyl group.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "heterocycle" refers to a monocyclic, bicyclic, tricyclic, or polycyclic systems, which are either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quaternized, including bicyclic, and tricyclic ring systems. The heterocycle may be attached via any heteroatom or carbon atom. Heterocycles include heteroaryls as defined above. Representative examples of heterocycles include, but are not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents.

"Heterocycloalkyl" denotes to a monocyclic or bicyclic ring system containing one or two saturated or unsaturated rings and containing at least one nitrogen, oxygen, or sulfur atom in the ring. The term "cycloalkyl" refers to a monocyclic or bicyclic ring system containing one or two saturated or unsaturated rings.

The term "haloalkyl," refers to a $C_1$-$C_8$ alkyl group wherein one or more hydrogen atoms in the $C_1$-$C_6$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" is employed here to refer to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term n-3, n-6, or n-9 polyunsaturated fatty acids (PUFA); n-3, n-6, or n-9 electrophilic fatty acid derivative (EFAD), respectively; or any of their respective metabolites is used interchangeably with the term ω-3, ω-6, or ω-9 polyunsaturated fatty acids (PUFA), respectively or ω-3, ω-6, or ω-9 electrophilic fatty acid derivatives (EFAD), respectively or its metabolites. Similarly, the term omega-3, omega-6, or omega-9 polyunsaturated fatty acids (PUFA), or omega-3, omega-6, or omega-9 electrophilic fatty acid derivatives (EFAD), or its metabolites, refers to the same.

In this context, the category of "metabolites" includes regioisomers, stereoisomers, and structural analogs of keto fatty acids. Thus, the inventive metabolites include fatty acids having tails of different carbon length, as well as positional isomers of the double bond. Also included within the class metabolites are positional isomers of the keto and hydroxy derivates of PUFA's. Additionally, the double bond can be a cis (Z) double bond or a trans (E) double bond. Pursuant to the invention, moreover, the metabolite category can encompass a small-molecule analog of a keto fatty acid, as described in greater detail below.

The term "derivative" refers to a compound that is derived from a similar compound, or a compound that can be imagined to arise from another compound, if one or more atoms are replaced with another atom or group of atoms. Derivatives of the fatty acid metabolites in accordance with the present invention include without limitation all compounds in which one or more carbon atoms in the fatty acid tail are substituted with oxygen, sulfur or amino groups. For example, the fatty acid tail can contain one of more polyethylene glycol units or one or more 1,2-diaminoethane units or combinations thereof.

The term "biological sample" refers to tissue, cells, cellular extract, homogenized tissue extract, a mixture of one or more enzymes in a suitable physiologically acceptable carrier, such as a mixture that includes without limitation the hydroxy dehydrogenases and cyclooxygenases.

The compound of the invention can also exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Certain compounds described here may have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6$^{th}$ ed. (Wiley, 2001) and DESIGN AND APPLICATION OF PRODRUGS (Harwood Academic Publishers Gmbh, 1985).

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The term "effective amount" refers to an amount of a compound of the invention or other active ingredient sufficient to provide a therapeutic or prophylactic benefit in the treatment or prevention of a disease or to delay or minimize symptoms associated with a disease. Further, a "therapeutically effective amount" with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

A "patient" or "subject" are used interchangeably throughout the specification and include an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

Electrophilic Fatty Acid Derivatives

Polyunsaturated fatty acids exert numerous beneficial health effects in humans. The major (n-3 PUFAs), are eicosapentanoic acid (EPA; (5Z,8Z,11Z,14Z,17Z)-eicosa-5,8,11,14,17-pentanoic acid) and docosahexanoic acid (DHA; (4E,7E,10Z,13E,16E,19E)-docosa-4,7,10,13,16,19-hexanoic acid). Both EPA and DHA exert anti-inflammatory effects by the competitive inhibition of arachidonic acid-derived prostanoid synthesis and subsequent production of n-3 prostanoids. In the context of the present invention, electrophilic fatty acid derivatives (EFAD's) are oxidative metabolites of n-3 PUFAs. Exemplary of an EFAD in accordance with this invention is an α,β-unsaturated keto fatty acid or its metabolites. Keto fatty acids are lipids in which the ketone group is on a carbon atom adjacent to the carbon-carbon double bond. Keto fatty acids and their biological metabolites exert biological effects by undergoing adduct forming reactions with nucleophiles present in the biological mileu.

Identification of Keto Fatty Acids and their Metabolites

The present inventors have discovered six electrophilic fatty acid derivatives (EFADs) produced in activated macrophages via a COX-2 dependent mechanism. However, acetyl salicylic acid (ASA) treatment of cells increased the rate of formation and intracellular concentration of EFAD's. These six EFADs were found at nM concentrations ranging from 65 nM to 350 nM in RAW264.7 and were also produced by LPS and IFNγ activated THP-1 cells and primary murine macrophages.

EFADs 1-3 were extensively characterized as α,β-unsaturated oxo-derivatives of the n-3 fatty acids DHA, (7Z,10Z,13Z,16Z,19Z)-docosa-7,10,13,16,19-pentaenoic acid (DPA), and docosatetraenoic acid (DTA) respectively. Specific 13-oxo and 17-oxo positional isomers have been identified for EFADs 1 and 2, and were synthesized in vitro. When their biological actions were investigated, EFADs were found to form adducts with proteins and small molecule cellular sulfhydryls, such as GSH, in activated RAW264.7 cells. The 17-oxo standards of EFAD-1 and EFAD-2 (17-oxoDHA and 17-oxoDPA) were able to activate PPARγ and the Keap-1/Nrf2 pathway and to inhibit iNOS and cytokine expression in activated macrophages at concentrations that paralleled the intracellular concentrations observed in activated macrophages.

In one embodiment the present invention describes a class of enzymatically generated electrophilic fatty acid derivatives (EFADs), or their enzymatically generated metabolites. The EFAD's and their metabolites have beneficial effects human health. According to the inventors the inventive keto fatty acids or their enzymatically generated metabolites, can inhibit inflammation by giving rise to adaptive signaling molecules in vivo. Since the nature of the response to an inflammatory condition depends on the cellular levels of a particular keto fatty acid, the development of an analytical method capable of identifying these agents in a biological sample are important. The present invention provides a mass spectrometric method for analyzing a biological sample. That is, the present method uses β-mercaptoethanol (BME)-driven alkylation of electrophilic compounds coupled with reverse phase-high pressure liquid chromatography tandem mass spectrometry (RP-HPLC-MS/MS)[22] method for identifying keto fatty acids and their metabolites.

Accordingly, a biological sample of interest is incubated with β-mercaptoethanol (BME) for a time sufficient to allow a Michael addition reaction between β-mercaptoethanol acting as a nucleophile and the fatty acid metabolites of formulae I, II or III being the electrophiles, with formation of a mixture containing one or more covalent β-mercaptoethanol-electrophilic fatty acid adducts. The identity of the keto fatty acid in the sample is deduced from the resultant mass peaks in a chromatogram of the sample. By applying this method to an in vitro model of inflammation, it was hypothesized that unknown or poorly characterized species that could be overlooked in traditional screening methods would be more prominently identified. The alkylation reaction with BME standardizes the MS/MS conditions for adducted RES conferring similar ionization and fragmentation properties on a range of RES, each with their own particular MS/MS characteristics. Accordingly, reversible RES free or adducted to protein or small molecule thiols, species that fragmented poorly during MS/MS, species that were in concentrations at or below the limits of detection, and species whose formation was not predictable based on current knowledge could be identified by this method.

As shown in FIG. 1, analysis of cellular lysates by the inventive method resulted in two peaks that showed a difference in mass of 78 daltons, which is attributed to the loss of the BME group (−78 amu; [M-BME]$^-$) from the adduct. The net result from such a fragmentation is a second peak whose mass will correspond to the mass of the keto fatty acid present in cellular lysate. Additional proof confirming the identity of the keto fatty acid is obtained by fragmenting the M-BME peak, followed by analysis of the resultant fragment ions. The advantage of the inventive method is that it provides a good leaving group (i.e., BME) which enhances the sensitivity and accuracy for the detection of a keto fatty acid in a biological sample.

Figure 5:
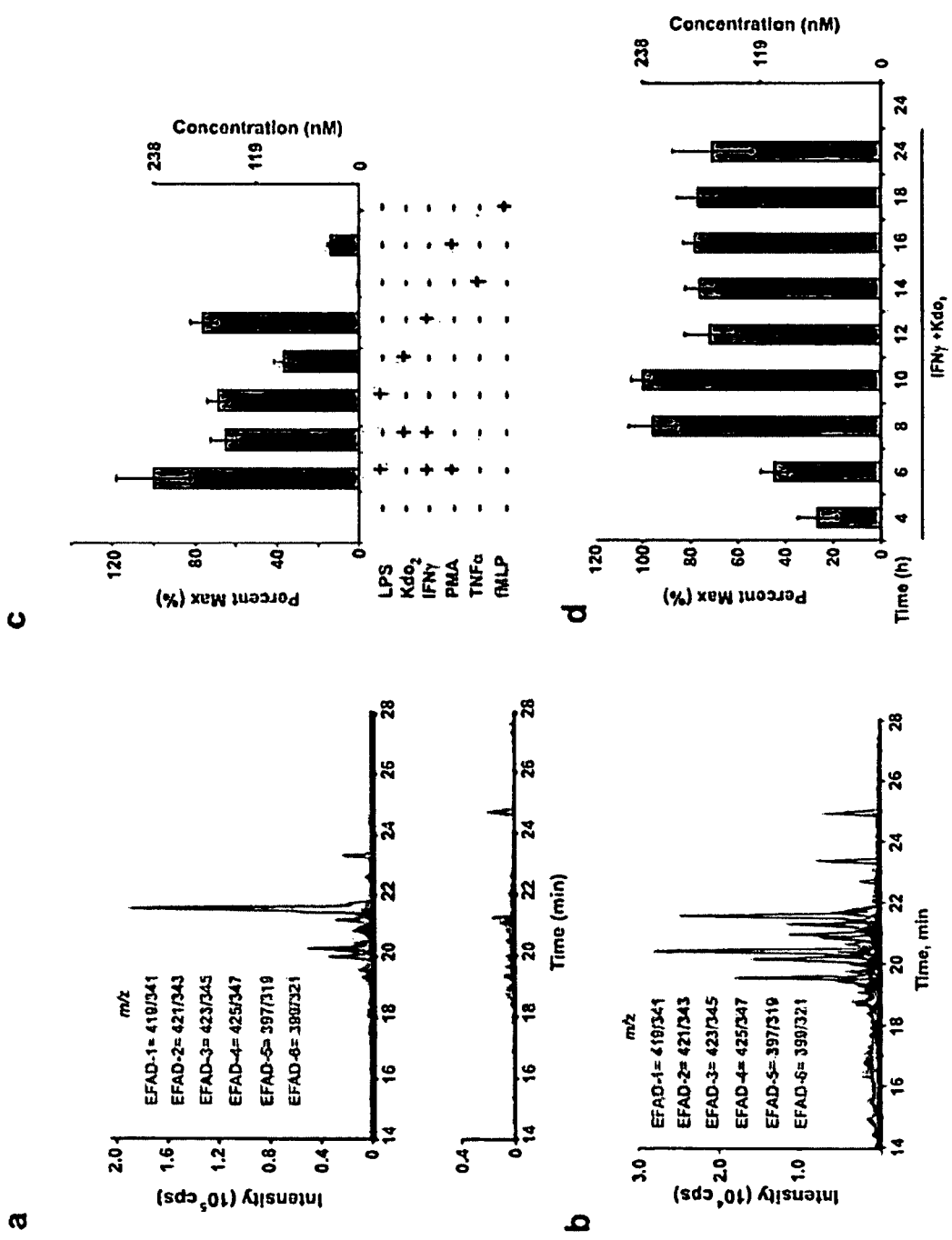
FIG. 5 illustrates production of EFAD's during macrophage activation. RAW264.7 cells were activated with PMA (3.24 μM), LPS (0.5 μg/ml), and IFNγ (200 U/ml) and harvested 20 h post activation. (a) MRM scans following the neutral loss of 78 (loss of BME) were used to detect electrophilic fatty acid adducted with BMB in cell extracts from activated (a, upper chromatogram) and non-activated (a, lower chromatogram) RAW 264.7 cells. (b) THP-1 cells were differentiated with PMA (86 nM) for 16 h, activated with $Kdo_2$ (0.5 μg/ml) and IFN-γ (200 U/ml), and EFAD levels were detected 8 h post activation. (c) RAW264.7 cells were activated with the indicated compounds and EFAD levels were quantified 20 h post activation. Compound concentrations are as follows: LPS (0.5 μg/ml), $Kdo_2$ (0.5 μg/ml), IFNγ (200 U/ml), PMA (3.24 μM), and fMLP (1 μM). Data are expressed as mean±S.D. (0=4), where *=significantly different ($p<0.01$) from "PMA+IFNγ+LPS," and #=a significant difference ($p<0.01$) between LPS and "$Kdo_2$+IFNγ" (one way ANOVA, post-hoc Tukey's test). (d) RAW264.7 cells were activated with Kdo2 (0.5 μg/ml) and IFNγ (200 U/ml) and EFAD levels were quantified at indicated times post activation. EFAD-2 levels are reported as generally representative for other EFADs.
Figure 12:
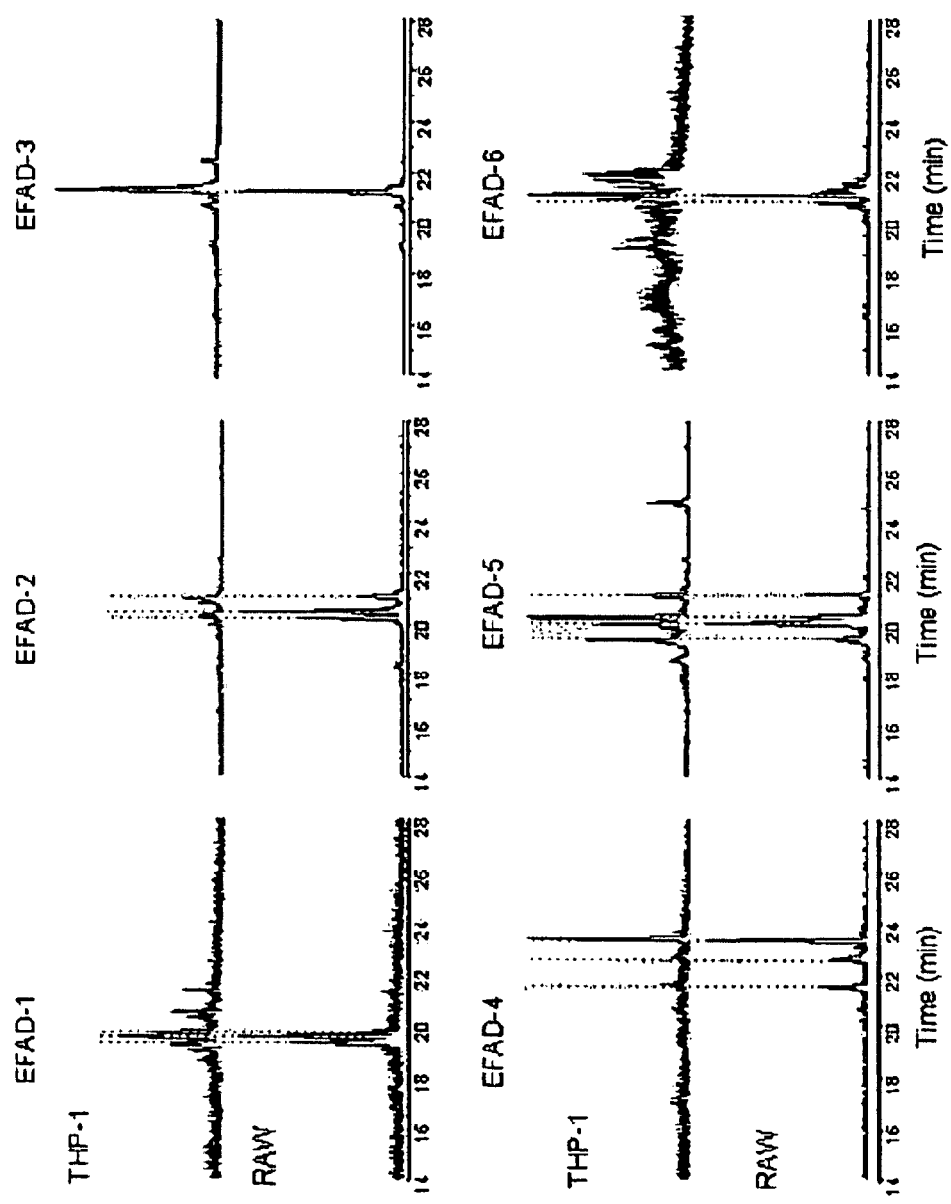
FIG. 12 illustrates EFADs produced by THP-1 cells coelute with those produced by RAW264.7. THP-1 cells were differentiated with PMA (86 nM) for 16 h, activated with $Kdo_2$ Lipid A (0.5 μg/ml) and IFNγ (200 U/ml). EFAD levels were detected 8 h postactivation. MRM scans following the neutral loss of 78 were used to detect EFAD-BME adducts.

Using this method six previously uncharacterized major RES species formed during activation of RAW 264.7 cells by PMA, LPS, and IFNγ (FIG. 5a) were identified. MS/MS experiments confirmed the neutral loss of BME from each of the six EFADS (data not shown). The same electrophilic species were detected in PMA, Kdo$_2$ and IFNγ-activated THP-1 cells, a human monocyte/macrophage cell line (FIGS. 5b and 12). Although their relative abundance differed between the two cell lines, MS/MS spectra showed the same characteristic losses and similar intensity ratios (data not shown).

Figure 13:
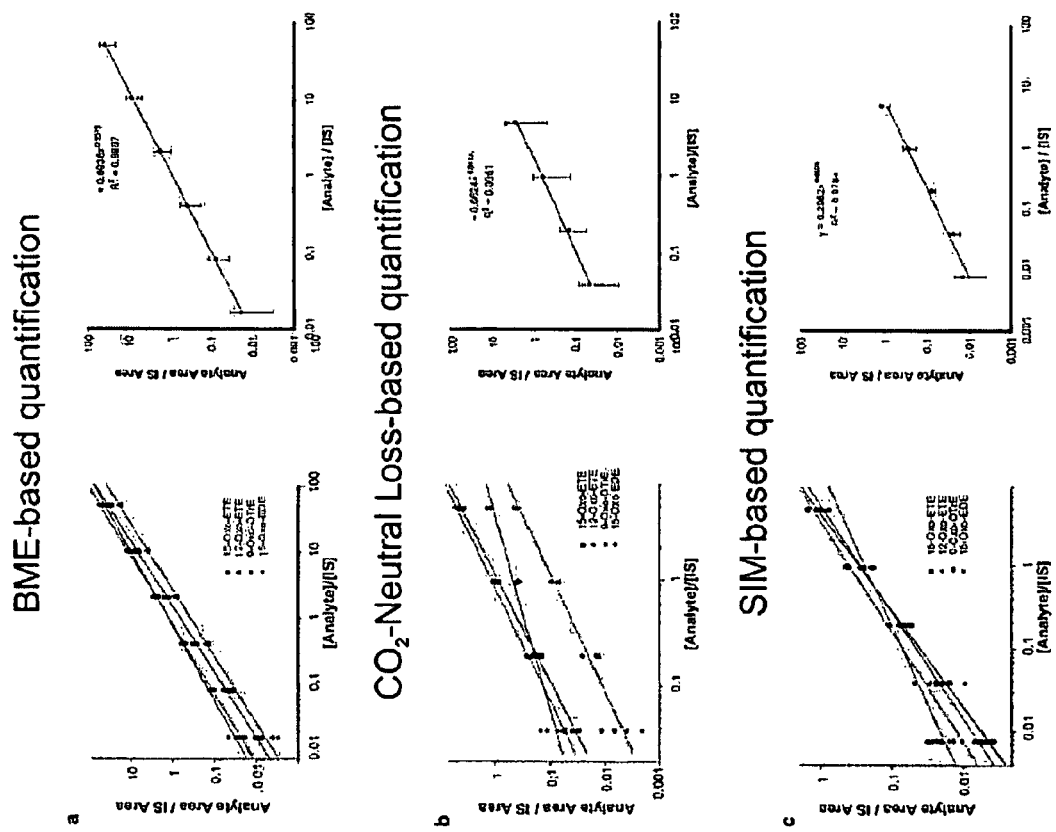
FIG. 13 illustrates that BME adducts of the α,β-unsaturated keto-derivatives yield the most reliable concentration curves for quantification by MS/M.S. (a) The compounds. 9-OxoODE. 12-OxoETE 15OxoEDE and 9-OxoOTrE were reacted with BME for 2 h and concentration curves were prepared by serial dilution in the presence of 5-OxoETE-d7 as internal standard; (b-c) Serial dilution of 9-OxoODE, 12-OxoETE, 15-OxoEDE and 9-OxoOTrE were quantified by MRM in the presence of internal standard (5-oxoETB-d7) following the neutral loss of $CO_2$ (b) or by S1M; (c) following parent mass. All peak areas corresponding to the compounds were normalized to the internal standard and plotted against their concentrations.
Figure 14:
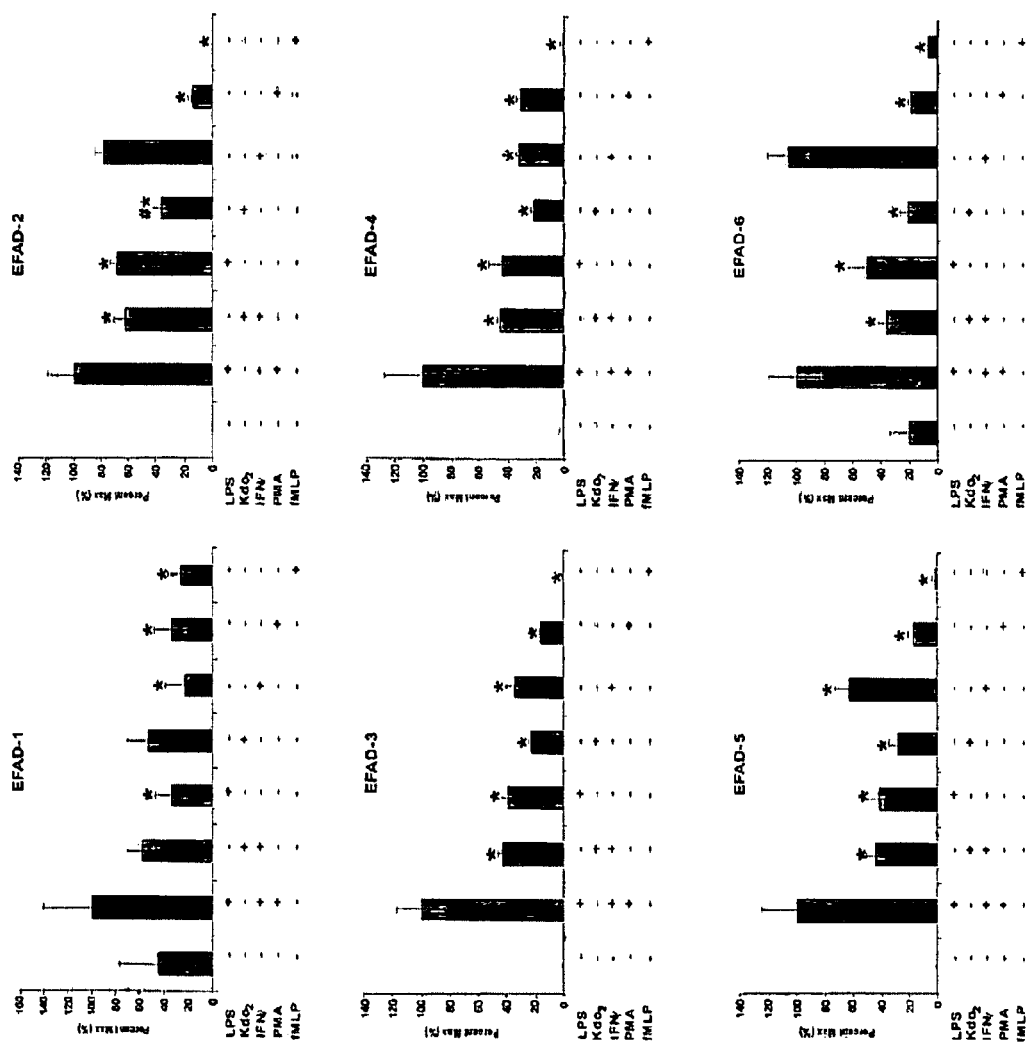
FIG. 14 illustrates that EFAD production is dependent on RAW264.7 cell activation. RAW24.7 cells were activated with the indicated compound and EFAD levels were quantified 20 h post activation. Compound concentrations are a follows: LPS (0.5 μg/ml) $Kdo_2$ Lipid A (0.5 μg/ml) IFNγ (200 U/ml), PMA (3.24 μM), and fMLP (1 μM). Data are expressed as mean±S.D. (n=4), where *=significantly different (p<0.01) from "PMA+IFNγ+LPS," and #=a significant difference (p<0.01) between LPS and "$Kdo_2$+IFNγ (one-way ANOVA, post-hoc Tukey s test).
Figure 15:
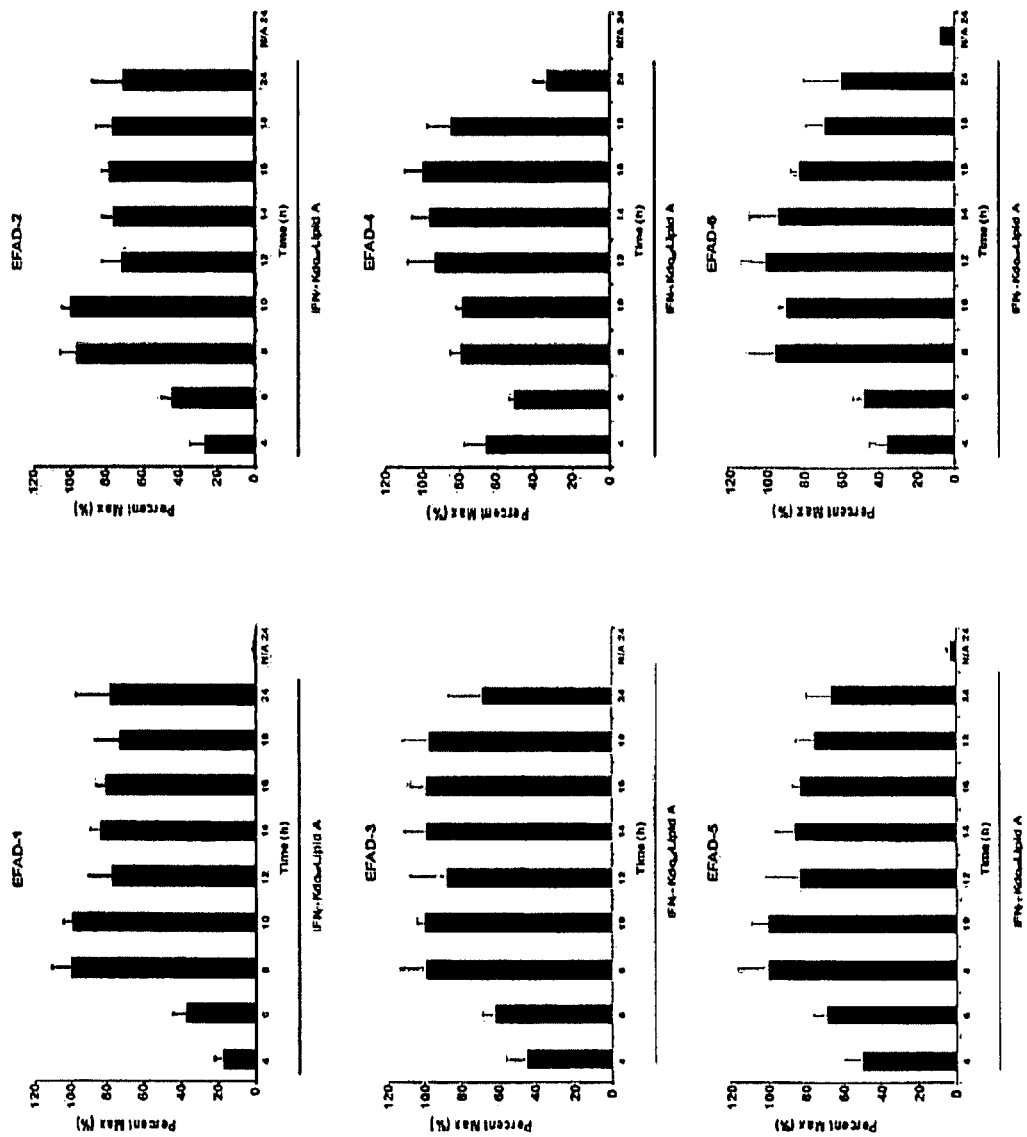
FIG. 15 illustrates EFAD production is time dependent. RA 264.7 cell were activated with $Kdo_2$ Lipid A (0.5 μg/ml), IFNγ (200 U/ml) and EFAD levels were quantified at indicated times post activation.

The robustness of the BME method for the detection and quantification of electrophilic lipids was further tested by comparing the mass spectrometric responses of different electrophilic fatty acids containing α,β-unsaturated moieties using the BME method, selected ion monitoring (SIM) and multiple ion monitoring (MRM) mode following the loss of $CO_2$ (FIG. 13). The standard deviation for the overall processes obtained for the different fatty acid at each concentration tested ranged from 40% to 50% for BME, 60-83% for MRM and 15-35% for SIM analysis. Moreover, the present inventors have found that the BME based mass spectrometric methodology was superior to other mass spectrum based methods as the former consistently gave a strong signal intensity, a low background level and linearity. The BME method was chosen for biological samples in which SIM and MRM analyses gave very poor results because of high background levels.

EFAD Formation is Time Dependent Following Macrophage Activation.

Figure 3:
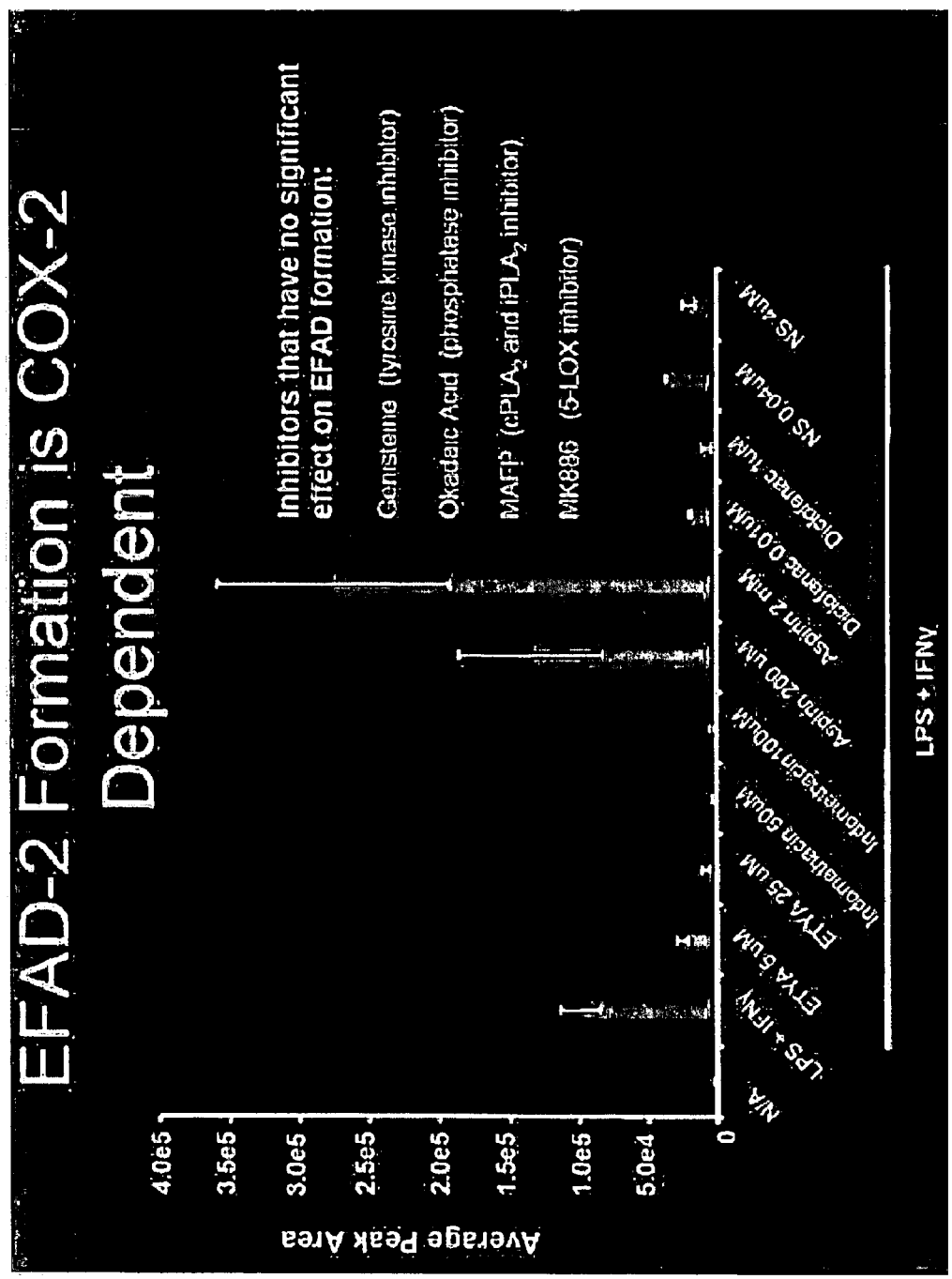
FIG. 3 shows the results from inhibition studies of COX-2. The results indicate that formation of electrophilic fatty acid is dependent on the level of COX-2.
Figure 4:
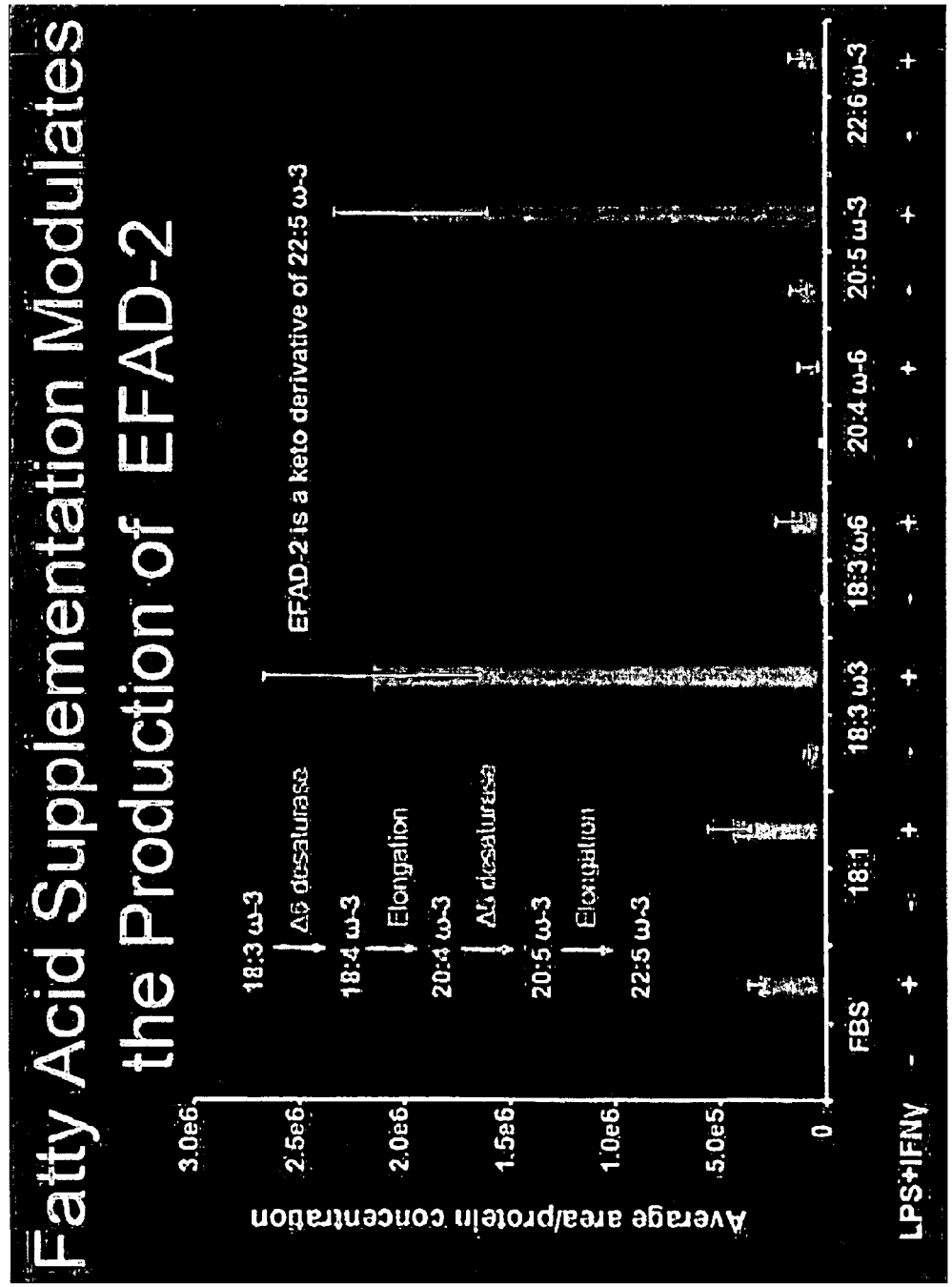
FIG. 4 is a graphical representation of the results of a fatty acid supplementation study in cells. It was discovered that the production of 22:5 ω-3 keto fatty acid involves a sequence of elongation and de-saturation steps using 18:5 ω-3 fatty acid as the starting material.

The formation of EFADs under different inflammatory conditions was confirmed by treating the cells with a variety of stimuli. Thus, macrophages were activated with various combinations of LPS, IFNγ, PMA, fMLP, and Kdo$_2$-Lipid A (Kdo$_2$) (FIG. 1c and Supplementary FIG. 3). Kdo$_2$, a synthetic endotoxin, was used to avoid the contribution of potential LPS preparation contaminants to EFAD formation. Since the combination of Kdo$_2$-Lipid A and IFNγ behaved nearly identically to LPS, it was used for all of the following experiments. This further confirmed that no components or contaminants in the LPS itself were acting as precursors of EFADs. Additionally, a time course analysis showed that EFAD formation started 4-6 h post activation and reached a peak at approximately 10 h (FIG. 1d and Supplementary FIG. 4). The profiles of time-dependent formation for the other EFADs were similar to that of EFAD-2 (data not shown) and the range of intracellular concentrations obtained for the different species ranged form 65 to 350 nM (Table 1).

EFADs are α,β-Unsaturated Oxo-Derivatives of n-3 Fatty Acids

Confirmation of the presence of an α,β-unsaturated ketone group in EFAD involved the identification was based on analysis of the mass-time of flight (TOF) data (at an accuracy below 10 ppm), elution profile, and base on the observance for the loss of $CO_2$ upon fragmentation of the EFAD. Thus, the EFAD of DPA (EFAD-2), was identified to be a mono-oxygenated derivative of a 22-carbon fatty acid tail having a total of five double bonds. The MS/MS spectrum for BME-adducted EFAD-2 (m/z 421 [M-H]$^-$) displayed characteristic fragment ions at m/z 403 ([M-H—H$_2$O]), 377 ([M-H—CO$_2$]), 343 ([M-H-BME]), 325 ([M-H-BME-H$_2$O]), and 299 ([M-H-BME-CO$_2$]) (FIG. 6a), consistent with the fragmentation pattern of BME adducts previously reported[22].

Figure 6:
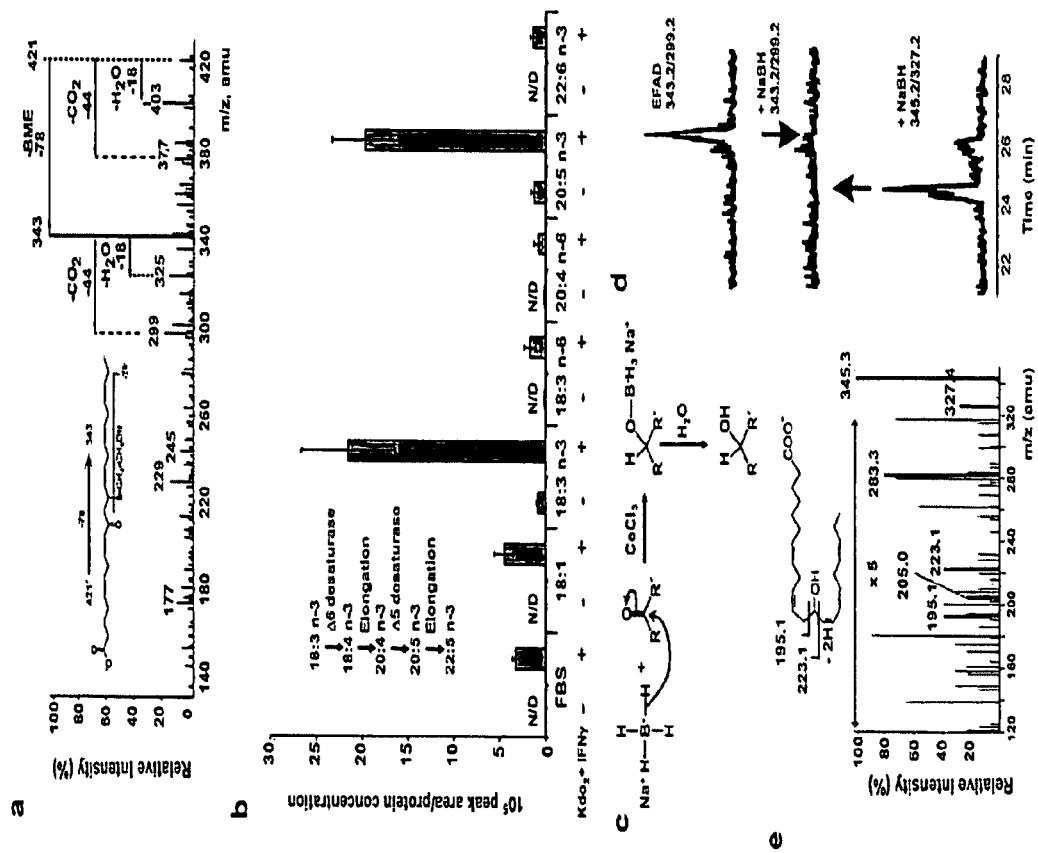
FIG. 6 shows that EFAD-2 is an α,β-unsaturated oxo-derivative of DPA. (a) A characteristic BME electrophile adduct fragmentation pattern showing the major neutral loss of 78 amu (corresponding to the loss of BME) is represented by the enhanced product ion analysis of EFAD-2. (b) RAW264.7 cells were grown for 3 days in DMEM and 10% FBS supplemented with 32 μM of the indicated fatty acid. On the third day cells were activated with $Kdo_2$ (0.5 μg/ml)) and IFNγ (200 U/ml) and EFAD-2 levels were quantified 20 h post activation. (c) Diagram of $NaBH_4$ reduction of oxo-group to an alcohol group. (d) MRM scans monitoring for the m/z transition of 343.2/299.2 (oxo-DPA losing $CO_2$) in RAW264.7 cell lysates purified for EFAD-2, non-treated or treated with $NaBH_4$ (upper and lower panel); MRM scans monitoring for the m/z transition of [345.2/327.2 (hydroxy-DPA/neutral loss of H20) in RAW264.7 cell lysates purified for EFAD-2 and treated with $NaBH_4$. (e) MS/MS fragmentation of EFAD-2 purified from activated RAW 264.7 cells and reduced with $NaBH_4$.

Similarly, the EFAD of DHA (EFAD-1) and the EFAD of DTA (EFAD-3), were identified as mono-oxygenated derivatives of a 22-carbon fatty acid with a total of six and four double bonds, respectively. To elucidate the precursors in vivo, fatty acid supplementation studies were performed. The formation of EFAD-2 was significantly increased in activated RAW264.7 cells supplemented with 18:3 n-3 (α-linolenic acid) and 20:5 n-3 (EPA) while formation was slightly decreased when the relevant n-6 species were provided (FIG. 6b). These results indicated that EFAD-2 was derived from n-3 PUFAs exclusively. Moreover, as illustrated in FIG. 4 EFAD-2 formation is COX-2 dependent. The supplementation of 22:6 n-3 (DHA) did not increase EFAD-2 levels. This was consistent with the fact that while mammalian cells can desaturate and elongate shorter chain PUFAs, they generally do not resaturate a PUFA such as DHA.

Figure 16:
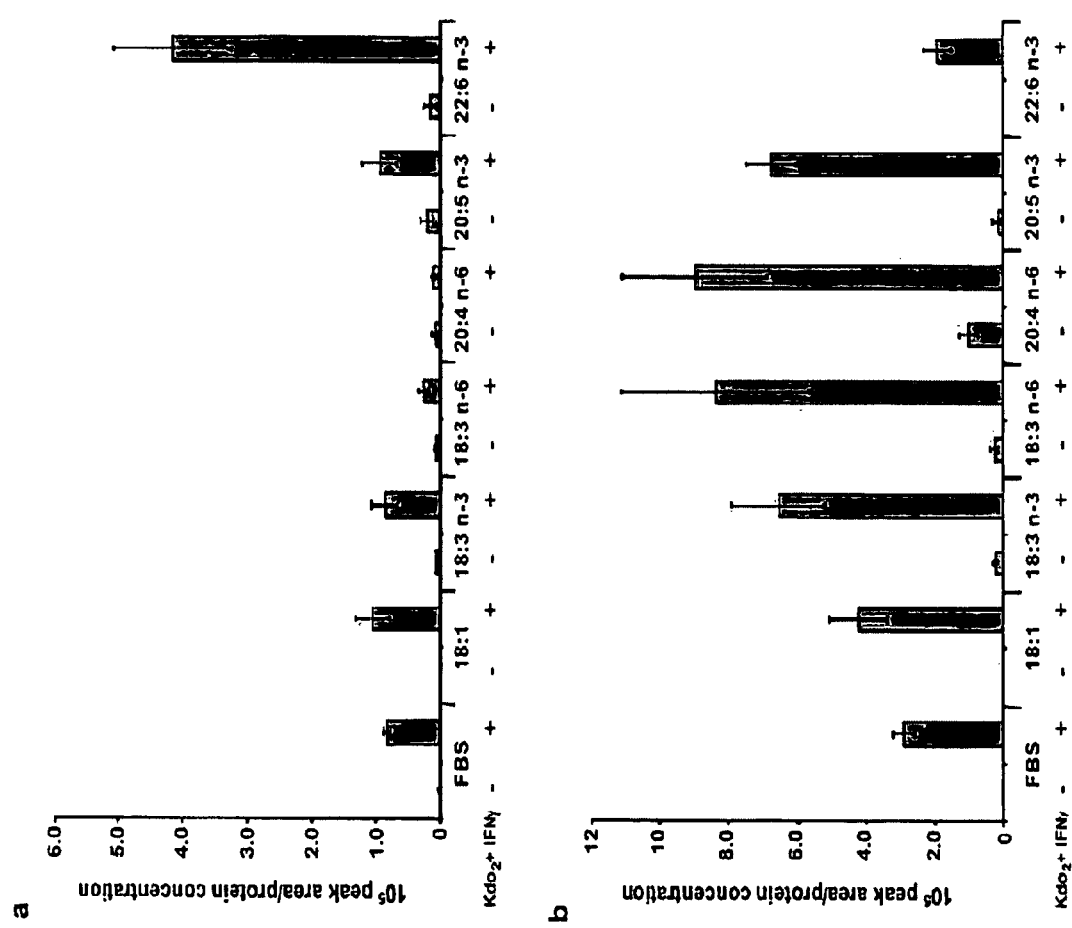
FIG. 16 illustrates that EFAD-1 and -3 are derived from the n-3 series of fatty acids. RAW264.7 cells were grown for 3 days in DMEM and 10% FBS supplemented with 32 μM of the indicated fatty acid. On the third day cells were activated with $Kdo_2$ Lipid A (0.5 μg/ml) and IFNγ (200 U/ml) and EFAD-1 and -3 levels were quantified 20 h post activation.

The formation of EFAD-1 in activated RAW264.7 cells was increased only by the supplementation of 22:6 n-3 (FIG. 16a). EFAD-3 was increased by both n-3 and n-6 fatty acid supplementation, indicating that its precursor could be either n-3 or n-6 DTA (FIG. 16b). Overall, this study showed that EFAD-1, EFAD-2, and a percentage of EFAD-3 were derivatives of n-3 fatty acids DHA, DPA and DTA while EFAD-4 to –6 were synthesized from n-3 and n-9 fatty acids (Table 1).

well as derivatives of these fatty acid metabolites candidate therapeutics for the treatment chronic pain and inflammation.

Keto Fatty Acids and Their Metabolites

The major n-3 polyunsaturated fatty acids (n-3 PUFAs) eicosapentanoic acid (EPA; (5Z,8Z,11Z,14Z,17Z)-eicosa-5, 8,11,14,17-pentanoic acid) and docosahexanoic acid (DHA; (4E,7E,10Z,13E,16E,19E)-docosa-4,7,10,13,16,19-hexanoic acid) have been associated with numerous beneficial health effects in humans. In particular, brain and retina tissues are enriched with DHA in healthy individuals and DHA is

TABLE 1

| Name | EFAD-1 | EFAD-2 | EFAD-3 | EFAD-4 | EFAD-5 | EFAD-6 |
|---|---|---|---|---|---|---|
| Cellular concentration nM | 65 ± 5 | 238 ± 16 | 348 ± 26 | 106 ± 6 | 326 ± 15 | 169 ± 18 |
| Mass (m/z) | 341.2 | 343.2 | 345.2 | 347.2 | 319.2 | 321.2 |
| FA precursors supporting formation | 22:6 | 18:3n-6, 20:5 | 20:4, 18:3n-6, 20:5, 18:3n-3 | 18:3n-6, 20:4 | 18:3n-6 | FBS, 18:1 |
| Series | ω-3 | ω-3 | ω-3 and ω-6 | ω-6 | ω-6 | ω-9 |
| Keto group present/position | 13- or 17- positon | 13- or 17- position | Yes | ? | Yes | ? |
| Formula | $C_{22}H_{29}O_3$ | $C_{22}H_{31}O_3$ | $C_{22}H_{33}O_3$ | ? | $C_{20}H_{31}O_3$ | $C_{20}H_{33}O_3$ |
| Identity | Keto-DHA | Keto-DPA | Keto-DTA | ω-6 derivative | Keto-20:3 | Keto-20:2 |
| Activated (Area/\|protein \|) ± SD | $8.2e^4 ± 0.55e^4$ | $3.3e^5 ± 0.38e^5$ | $2.9e^5 ± 0.32e^5$ | $7.5e^4 ± 0.53e^4$ | $1.7e^5 ± 0.11e^5$ | $2.8e^5 ± 0.24e^5$ |
| +ETYA (↓COX) | ↓ | ↓ | ↓ | ↓ | ↓ | ↓ |
| +Aspirin (↓COX) | ↑ | ↑ | ↑ | ↓ | ↑ | ↓ |
| +Ibuprofen (↓COX) | ↓ | ↓ | ↓ | ↓ | NE | ↓ |
| +Indomethacin (↓COX) | ↓ | ↓ | ↓ | ↓ | ↓ | ↓ |
| +Diclofenac (↓COX) | ↓ | ↓ | ↓ | ↓ | ↓ | ↓ |
| +Celecoxib (↓COX) | ↓ | ↓ | ↓ | ↓ | ↓ | ↓ |
| +Genisteine | ↓ | ↓ | ↓ | ↓ | ↓ | ↓ |
| +MAFP (↓PLA₂) | ↓ | ↓ | ↓ | ↓ | ↓ | ↓ |
| +MK886 (↓5-LOX) | NE | NE | NE | NE | NE | NE |
| +OKA | NE | NE | NE | NE | NE | NE |

Further confirmation that the electrophilic functional group of EFADs was an α,β-unsaturated carbonyl and to exclude the presence of other electrophilic groups (e.g., epoxy group), in the fatty acid tail was obtained by performing the Luche reaction (FIG. 6c). This reaction uses $NaBH_4$ (in the presence of $CeCl_3$) to selectively reduce carbonyl groups (but not epoxy or carboxylic acid groups) to the allylic alcohol without loss of regioselectivity[23]. Lipid extracts from IFNγ and LPS-activated RAW264.7 cell lysates were fractionated by HPLC. The fraction containing EFAD-2 was purified and reduced with $NaBH_4$ resulting in a significant decrease of the signal corresponding to EFAD-2 and the appearance of a previously absent peak at the transition 345/327 (reduced product of EFAD-2, FIG. 6d). Due to the enhanced fragmentation typically induced by hydroxygroups during MS/MS, products of the Luche reaction yielded relevant information about the location of the carbonyl group. Accordingly, in addition to the commonly observed ion fragments (m/z 327 ([M-H]-$H_2O$) and 283 ([M-H]-$H_2O$—$CO_2$), the following diagnostic ions for β-hydroxy-DPA (13-OH-DPA) were observed in the EFAD-2 enriched fraction reduced with $NaBH_4$: m/z 223, 205 (223-$H_2O$) and 195 (FIG. 6e). These findings finally revealed that EFAD-2 corresponded to 13-oxoDPA and that EFAD-3 was an oxo-derivative of DTA. (Table 1)

The BME technique is useful to identify the biologically important metabolites of electrophilic keto fatty acids. For example, the BME technique was used by the inventors to fish out the biologically active C-10 to C18 metabolites which are potent anti-inflammatory electrophilic signaling molecules. The small, low molecular weight metabolites have improved stability and bio-availability, making these compounds as necessary for the normal development and function of these tissues[1,2]. Moreover, the consumption of DHA in the diet has been implicated in reducing neurocognitive decline[3], improving insulin resistance in diabetics[4], decreasing incidence of cardiovascular risks such as myocardial infarction[5], and reducing inflammation[6]. Both EPA and DHA exert anti-inflammatory effects by competitive inhibition of arachidonic acid-derived prostanoid synthesis, and subsequent production of n-3 prostanoids with the ability to induce vasodilation, inhibit platelet aggregation[7] and promote a series of anti-inflammatory events whose mechanisms remain to be elucidated.

Several emerging classes of anti-inflammatory lipid mediators have been recently reported. Although structurally related to pro-inflammatory prostanoids, these lipid derivatives promote resolution of inflammation by suppressing NF-κB activation, modulating cytokine expression, activating G-protein coupled receptors[8] and promoting cyto-protective responses[9]. Among these are the enzymatically synthesized resolvins (Rvs), neuroprotectins, maresins, and lipoxins (LXs). Oxygenases, including cyclooxygenase-2 (COX-2) and lipoxygenases (LOXs), are involved in these biosynthetic processes emerging as key enzymes both in the onset of inflammatory events and in their finely orchestrated resolution[10].

A second group of such lipid derivatives include nitro-fatty acids ($NO_2$-FAs), 15-deoxy-Δ(12,14)-prostaglandin $J_2$ (15d-$PGJ_2$), and neuroprostanes which are reactive electrophilic species (RES) mostly formed during non-enzymatic oxidative events. In the context of this invention, electrophilic fatty acid derivatives (EFAD's), are oxidative metabolites of n-3 PUFAs. Exemplary of an EFAD is a keto fatty acid. Keto fatty acids are lipids in which there is a ketone group adjacent to the carbon atoms of the double bond. Keto fatty acids as well as their biological metabolites are reactive electrophilic species (RES), that exert their biological effects mainly via electrophilic reactions[11,12].

RES are molecules characterized by having an electron-withdrawing functional group that renders the α-carbon electron-poor and reactive towards electron-rich donor molecules (nucleophiles). The strength of the electron withdrawing group will determine the reactivity of the electrophile. Exemplary of an electron withdrawing group present in the inventive keto fatty acids or their metabolites is an α,β-unsaturated carbonyl group which can undergo a Michael addition reaction with biological nucleophiles. A more detailed characterization of RES is presented below herein.

Thus, when inflammation is initiated in mouse cells (RAW264.7) and human monocyte cells (THP-1), respectively, intracellular levels of keto fatty acid are elevated. In particular, six electrophilic fatty acid derivatives (EFADs) were identified in activated macrophages by the present inventors. These EFADS in activated macrophages were characterized by mass spectrometry as α,β-unsaturated oxo-derivatives of the n-3 fatty acids DHA, (7Z,10Z,13Z,16Z,19Z)-docosa-7,10,13,16,19-pentanoic acid (DPA), and docosatetranoic acid (DTA) respectively. Specifically 13-oxo and 17-oxo positional isomers have been identified for the DHA and DPA EFADs.

Biological Production of EFAD

1. Role of COX-2

Figure 7:
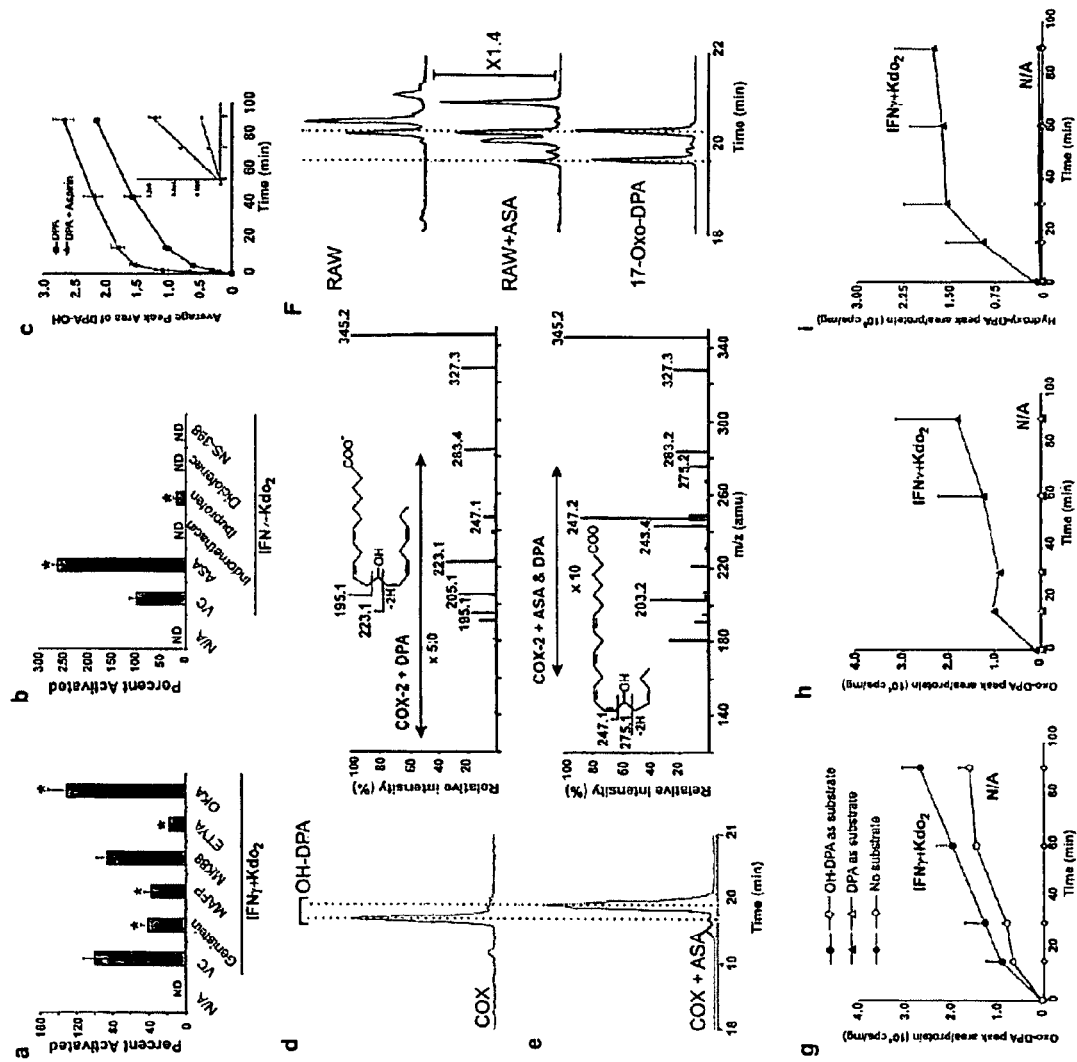
FIG. 7 shows that EFAD-2 formation is dependent on COX-2 activity. RAW264.7 cells were activated with $Kdo_2$ (0.5 μg/ml) and IFNγ (200 U/ml) in the presence of the indicated inhibitors and EFAD-2 levels were quantified 20 h post activation. (a) Inhibitor concentrations were as follows: genistein (25 μM), MAFP (25 μM), MK886 (500 nM), ETYA (25 μM) and OKA (50 nM). (b) COX inhibitor concentrations were as follows: ASA (200 μM), indomethacin (25 μM), ibuprofen (100 μM), diclofenac (1 μM) and NS-398 (4 μM). Data are expressed as mean±S.D. (n=4), where *=significantly different ($p<0.01$) from "$Kdo_2$+IFNγ" (one-way ANOVA, post-hoc Tukey's test). (c) The hydroxy-precursors of EFAD-2 were synthesized using purified ovine COX-2+DPA, ±ASA and quantified (MRM 345/327) at the indicated time points. (d, e) Chromatographic profiles (left panels) and spectra (right panels) of the two isomers formed by COX-2 and COX-2+ASA. (f) RAW264.7 cells were activated with $Kdo_2$ (0.5 mg/ml) and IFNγ (200 U/ml)±ASA and the production of oxoDPA was analyzed and compared to a 17-oxoDPA standard. The elution profile of EFAD-2 was monitored by MRM scans following the m/z transition of 421.2/343.2 (the BME adduct of EFAD-2 losing BME). (g-i) RAW264.7 cells were activated with $Kdo_2$ (0.5 μg/ml) and IFNγ (200 U/ml) or treated with vehicle control and lysates were collected 20 h post activation. OH-DPA (μM), DPA (μM), or vehicle was added to the cell lysates and the production of oxo-DPA or OH-DPA was monitored over time. Full and empty symbols indicate the use of cell lysates from, respectively, activated and non-activated cells.
Figure 17:
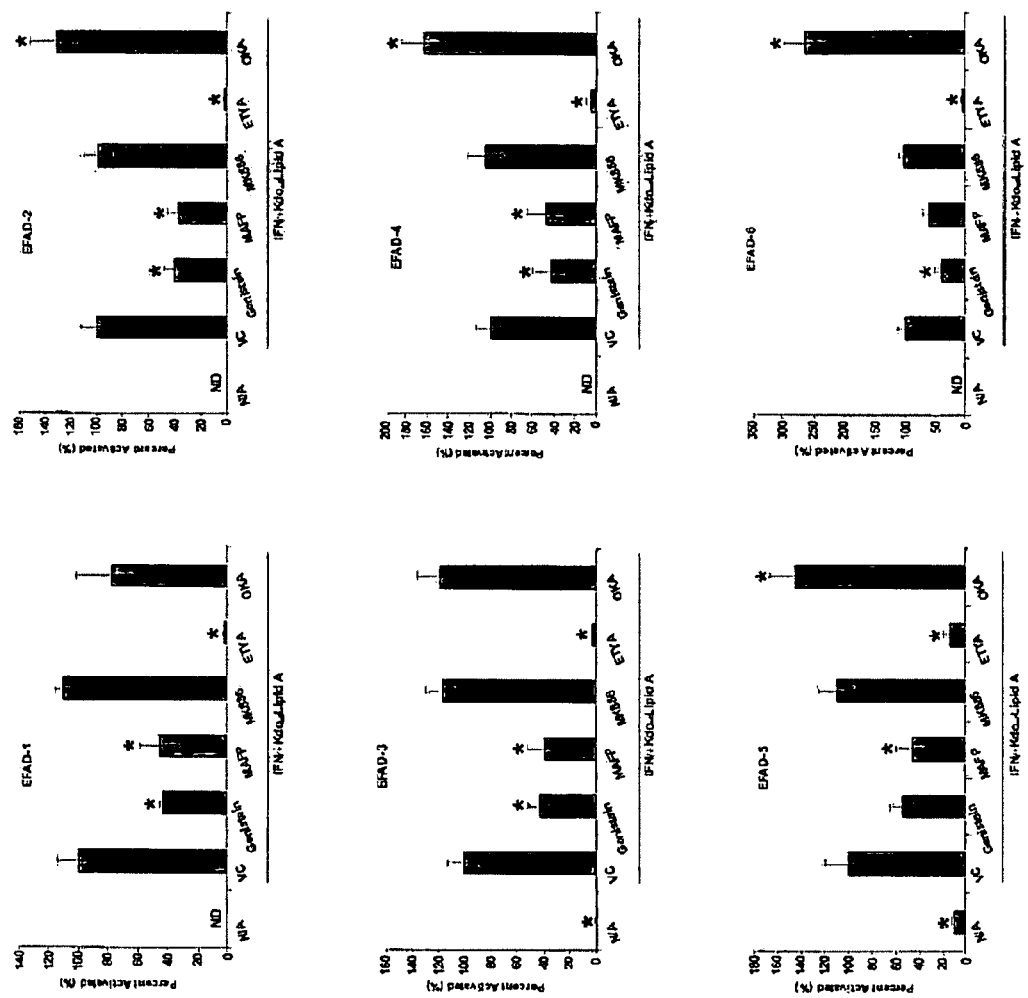
FIG. 17 illustrates that EFAD formation is dependent on $PLA_2$ and COX-2 activity. RAW264.7 cells were activated with $Kdo_2$ Lipid A (0.5 μg/ml) and IFNγ (200 U/ml) in the presence of the indicated inhibitors and EFAD-2 levels were quantified 20 h post activation. Inhibitor concentrations were as follows: genistein (25 μM), MAFP (25 μM), MK886 (500 nM), ETYA (25 μM) and OKA (50 nM). Data are expressed as mean±S.D. (n=4), where *=significantly different (p<0.01) from "$Kdo_2$+IFNγ" (one-way ANOVA, post-hoc Tukey s test).

Not wishing to be bound by any particular theory, the present inventors believe that the EFAD's are produced in activated cells via a COX-2 dependent mechanism. For example, in the process of identifying EFADs as α,β-unsaturated oxo-derivatives of PUFAs, a series of experiments were performed to determine the pathways involved in their synthesis. EFAD levels were quantified in RAW264.7 cells activated with $Kdo_2$ and IFNγ and treated with a variety of inhibitors (FIGS. 7a, FIG. 17, and Table 1).

Both genistein and methyl arachidonyl fluorophosphonate (MAFP) inhibited EFAD production by over 50%. Genistein was chosen as a general tyrosine kinase inhibitor to inhibit LPS and IFNγ signal transduction. MAFP, a selective irreversible inhibitor of both calcium-dependent and calcium-independent cytosolic phospholipase A2 ($cPLA_2$ and $iPLA_2$), was employed to determine if EFAD precursors were released from the cytoplasmic membrane upon RAW264.7 cell activation. To determine if 5-lipoxygenase (5-LOX) was involved in EFAD formation, MK886 was used to prevent FLAP-dependent activation of 5-LOX. MK886 had no significant effect on EFAD.

Figure 18:
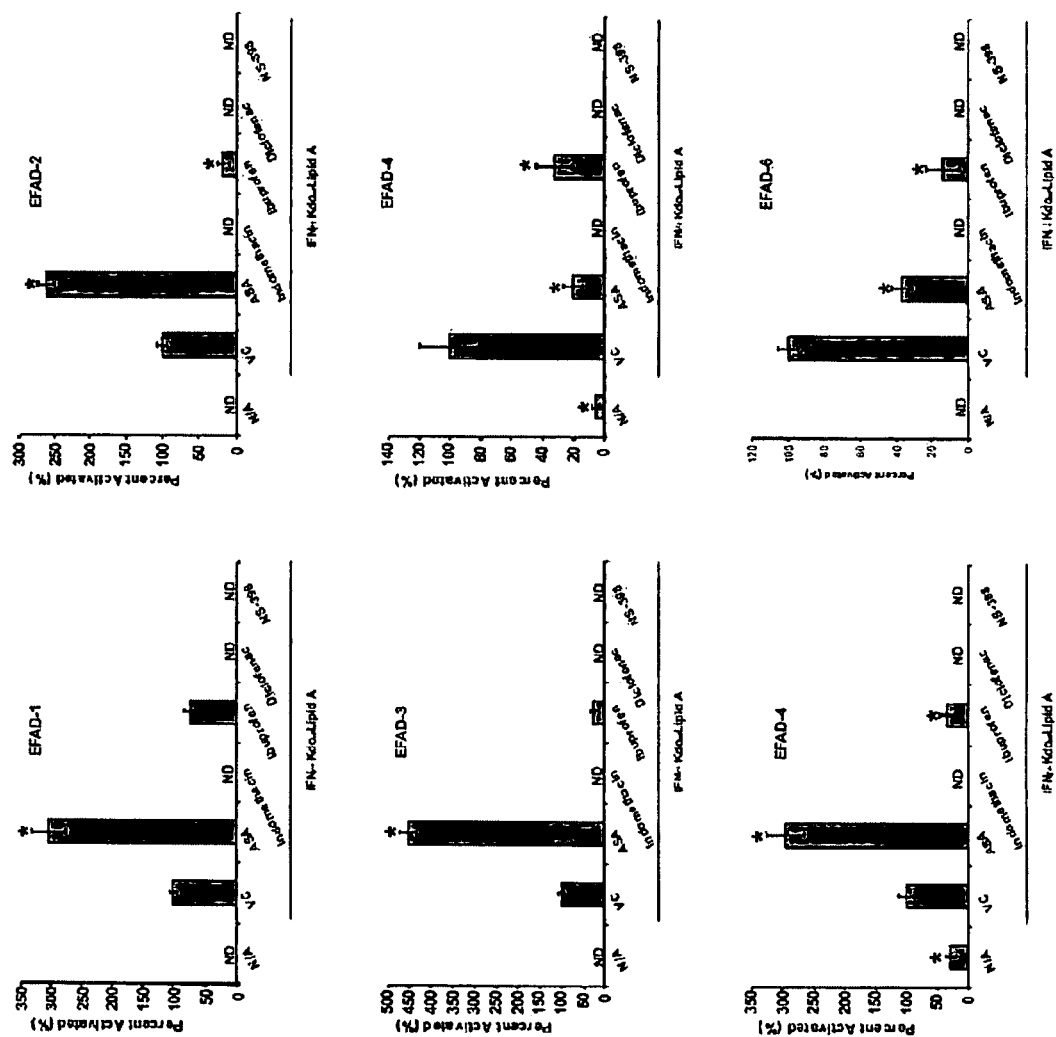
FIG. 18 illustrates that EFAD formation is dependent on $CO_2$ activity. RAW264.7 cells were activated with $Kdo_2$ Lipid A (0.5 μg/ml) and IFN-γ (200 U/ml) in the presence of the indicated inhibitors and EFAD-2 levels were quantified 20 h post activation. COX inhibitor concentrations were as follows: ASA (200 μM), indomethacin (25 μM). ibuprofen. μM), diclofenac (1 μM) and NS-398 (4 μM). Data are expressed as mean±S.D. (n=4), where *=significantly different (p<0.01) from "$Kdo_2$+IFNγ" (one-way ANOVA, post-hoc Tukey s test).

Eicosatetraynoic acid (ETYA), a nonspecific inhibitor of COX and LOX enzymes, was found to strongly inhibit EFAD formation, while the general phosphatase inhibitor, okadaic acid (OKA), caused a slight increase in EFAD formation, probably due to the enhancement of LPS and IFNγ signal transduction. In order to determine whether the inhibitory effect of ETYA on EFAD formation was due specifically to the inhibition of COX, EFAD levels were quantified in RAW264.7 cells that were activated with $Kdo_2$ and IFNγ, and treated with COX inhibitors at concentrations that were at least 5 times their $IC_{50}$ values[24] (FIGS. 7c, and 18, and Table 1).

Indomethacin and diclofenac were found to completely abolish EFAD formation, while ibuprofen was found to significantly inhibit EFAD formation by more than 80%, with the exception of EFAD-1, which showed no significant effect. Moreover, the selective COX-2 inhibitor NS-398, a close structural relative of Nimesulide, abolished EFAD formation as well. That is, COX-2 specific conventional non-steroidal anti-inflammatory drugs (NSAIDs) used to reduce inflammation also reduce the resultant levels of cellular keto fatty acids. See FIG. 3.

Finally, acetyl salicylic acid (ASA), significantly increased EFAD formation by about 2.5 fold for all EFADs, with the only exception being EFAD-4 and EFAD-6. This was consistent with previous reports showing that ASA acetylation of COX-2 Ser530 favors the formation of mono-oxygenated derivatives of long chain PUFAs[25]. A summary of the results obtained with the inhibitor study for all EFADs is reported in Table 1.

Figure 19:
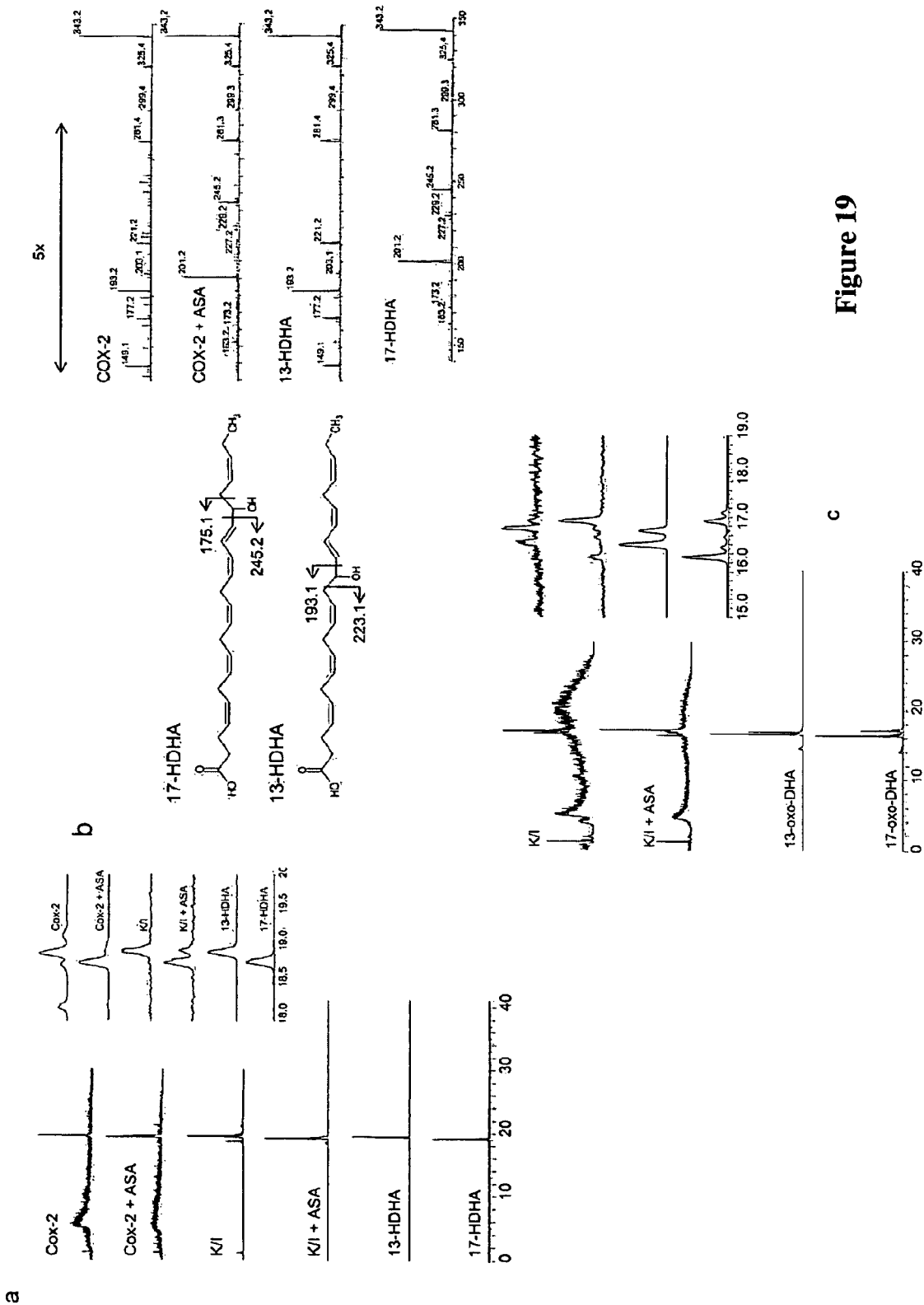
FIG. 19 illustrates that aspirin-acetylated COX-2 produces 17-HDHA, rather than 13-HDHA, both in vivo and in vitro. Chromatographic profiles (a) and mass spectra (b) of HDHA synthesized by COX-2 in presence of 10 μM DHA±ASA. Chromatographic profiles of HDHA from cellysates of activated RAW264.7 cells (K/I)±ASA were also compared with 13-HDHA and 17-HDHA synthetic standards. (c) Chromatographic:profiles of oxoDAH generated by activated RAW264.7 cells (K/I)±ASA compared with 13-oxoDHA and 17-oxoDHA synthetic standards. Enlarged chromatograms are reported in the insets.

The results of the COX-2 inhibition study implicate a the involvement of COX-2 in EFAD formation and motivated the development of an in vitro model of enzymatic EFAD synthesis. Purified ovine COX-2 was used to generate the EFAD-2 precursor (OH-DPA), (FIG. 7c-e), while the EFAD-1 precursor, hydroxy-DHA (OH-DHA), was produced from DHA by COX-2 (FIGS. 19a and 19b). Interestingly, ASA increased the rate and extent of formation of OH-DPA (FIG. 7c) and shifted the population of hydroxy-isomers produced from 13- to 17- (FIG. 7d-f and FIGS. 19a and 19b).

Analysis of the enzymatic reaction mixture using mass spectrometry showed a characteristic fragmentation pattern. For the fragmentation pattern of COX-derived 13-OH-DPA characteristic m/z 195 and 223 ions were observed, which ions correspond to the hydroxyl group induced fragmentation observed for RAW264.7 cell extracts that were subjected to a reduction reaction using sodium borohydride ($NaBH_4$) (FIGS. 6e and 7d). In contrast, when COX-2 reaction mixture was treated with ASA, characteristic ions corresponding to a hydroxyl group at C-17 position were detected (FIG. 7e). In activated, ASA-treated RAW264.7 cells this shift resulted in the production of 17-oxo-isomers, as shown in FIG. 7g for EFAD-2 and FIG. 19c for EFAD-1.

2. Role of Hydroxydehydrogenases

The conversion of PUFA's to their corresponding oxo-derivatives requires the presence of hydrodehydrogenases in addition to COX-2. For example, lysates from activated or non-activated RAW264.7 cells were incubated with the EFAD-2 precursors DPA and OH-DPA. When activated and non-activated cell lysates were incubated with OH-DPA in presence of $NAD^+$ there was a time-dependent production of EFAD-2 (FIG. 7g). In contrast, only lysate from activated cells displayed a time-dependent production of OH-DPA and EFAD-2 when incubated with DPA (FIG. 7g-i).

These results show that only activated cells are able to metabolically convert DPA into its oxo derivative (oxo-DPA), confirming the role of COX-2 in the conversion of PUFA's to their corresponding hydroxy derivatives which are converted to the corresponding oxo derivatives enzymatically via hydroxy-dehydrogenases that appear to be constitutively expressed. According to the present inventors, therefore, a linear correlation exists between the in vivo levels of a keto fatty acid and the in vivo level of COX-2. The formation of EFAD's in other cell lines such as primary cell lines was also determined by the present inventors as further explained below in the experimental section.

EFADs Activate Cyto-Protective and Anti-Inflammatory Pathways

Figure 11:
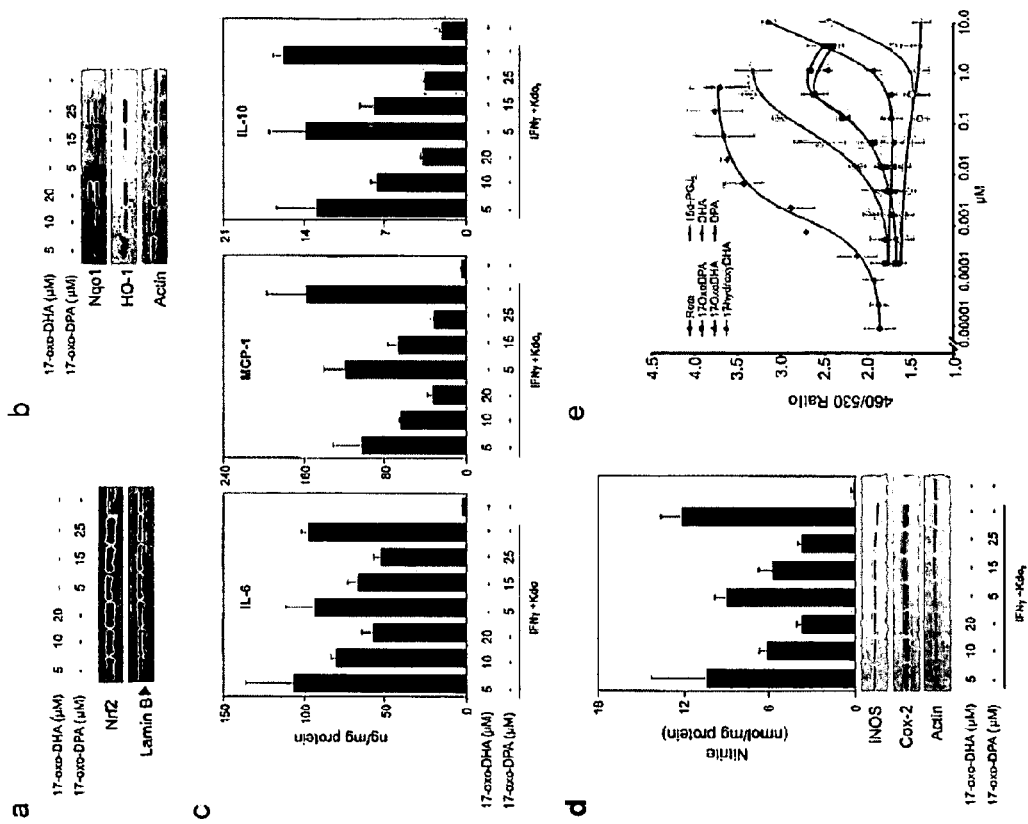
FIG. 11 illustrates modulation of anti-oxidant and inflammatory responses by 17-oxoDHA and 17-oxoDPA. RAW264.7 cells were treated with increasing concentration of 17-oxoDHA and 17-oxoDPA. (a) Cells were harvested 1 h after treatment and Nrf2 levels were quantified in nuclear extracts. (b) Cells were harvested 18 h after treatment and HO-1 and Nqo1 (upper band) levels were measured by western blot. (c, d) RAW264.7 cells were treated with increasing concentration of 17-oxoDHA and 17-oxoDPA for 6 h and $Kdo_2$+IFNγ were added. Samples were collected at 12 h. IL-6, MCP-1 and IL-10 levels were measured in the cell media by Quantikine ELISA Kit (R&D Systems) and normalized by the total protein content (c); Nitrite levels were measured in the cell media and normalized by the total protein content and iNOS and Cox-2 levels were measured in total cell lysates (d); (e) PPARγ beta-lactamase reporter assays were performed for Rosiglitazone, 17-OxoDPA, 17-OxoDHA, 15d-$PGJ_2$, 17-hydroxyDHA, DPA, and DHA with concentrations ranging from 0.5-10,000 nM.

As described above, compounds of the invention can react with biological thiols to form reversible covalent adducts. Thus, intracellular RES's such as EFAD's promote the activation of the Nrf2-dependent anti-oxidant response pathway via thiol-dependent modification of the Nrf2 inhibitor Keap1. This induces nuclear translocation of the transcription factor Nrf2 and the expression of its target genes[28]. For example, the 17-oxoDHA and 17-oxoDPA promoted dose-dependent Nrf2 nuclear accumulation and expression of the cytoprotective enzymes heme oxygenase 1 (HO-1) and NAD(P)H:quinone oxidoreductase 1 (Nqo1) (FIGS. 11a and 11b).

To investigate whether the 17-oxo DHA and 17-oxo DPA played a role in modulating the inflammatory response generated by Kdo$_2$ and IFNγ, the present investigators study the change in levels of cytokines, IL-6, MCP-1 and IL-10 in cells exposed to increasing doses of 17-oxo DHA and 17-oxo DPA.

Figure 23:
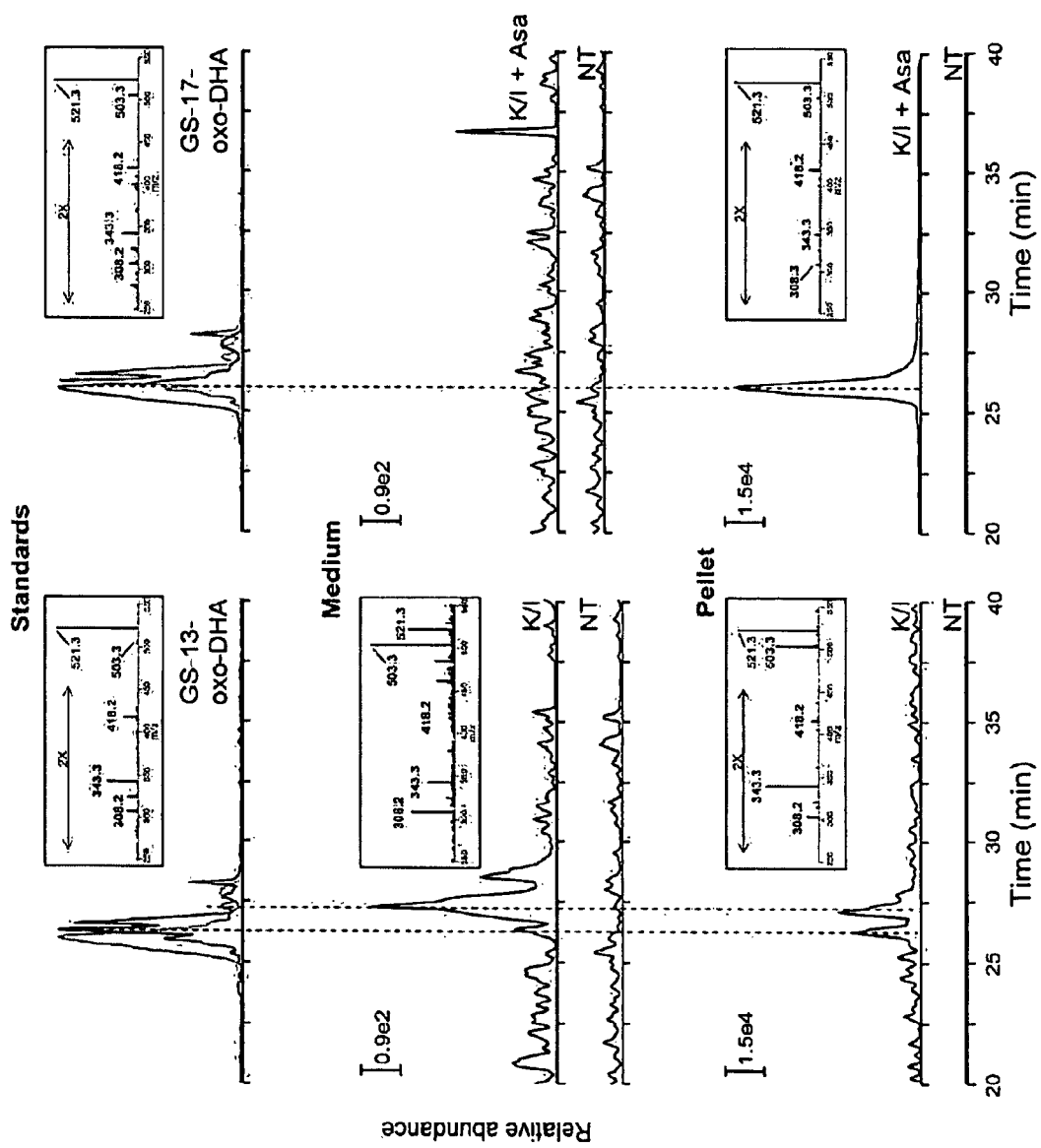
FIG. 23 illustrates that GS-oxoDHA adducts are detected in pellets and media of activated RAW264.7 cells. Chromatographic profiles and mass spectra of 13 and 17-oxoDHA derived from synthesized standards (upper panels) cell medium (middle panel) and cell pellet (lower panel). Differences due to recovery efficiency were taken into account by correcting the signal levels using the internal standard GS-5-oxoETE-d7. Fragments 343.3 and 521.3 were selected and monitored as the ones giving the best signal to noise ratio in samples derived from cell media and cell pellets, re peerively. Fragments 521.3 and 418.2 corresponded to fragments y2 and c1, while 343.3 and 308.2 derived from the lipid and the glutathione molecule. Fragment 503.3 derived from loss of water from 523.3.
Figure 24:
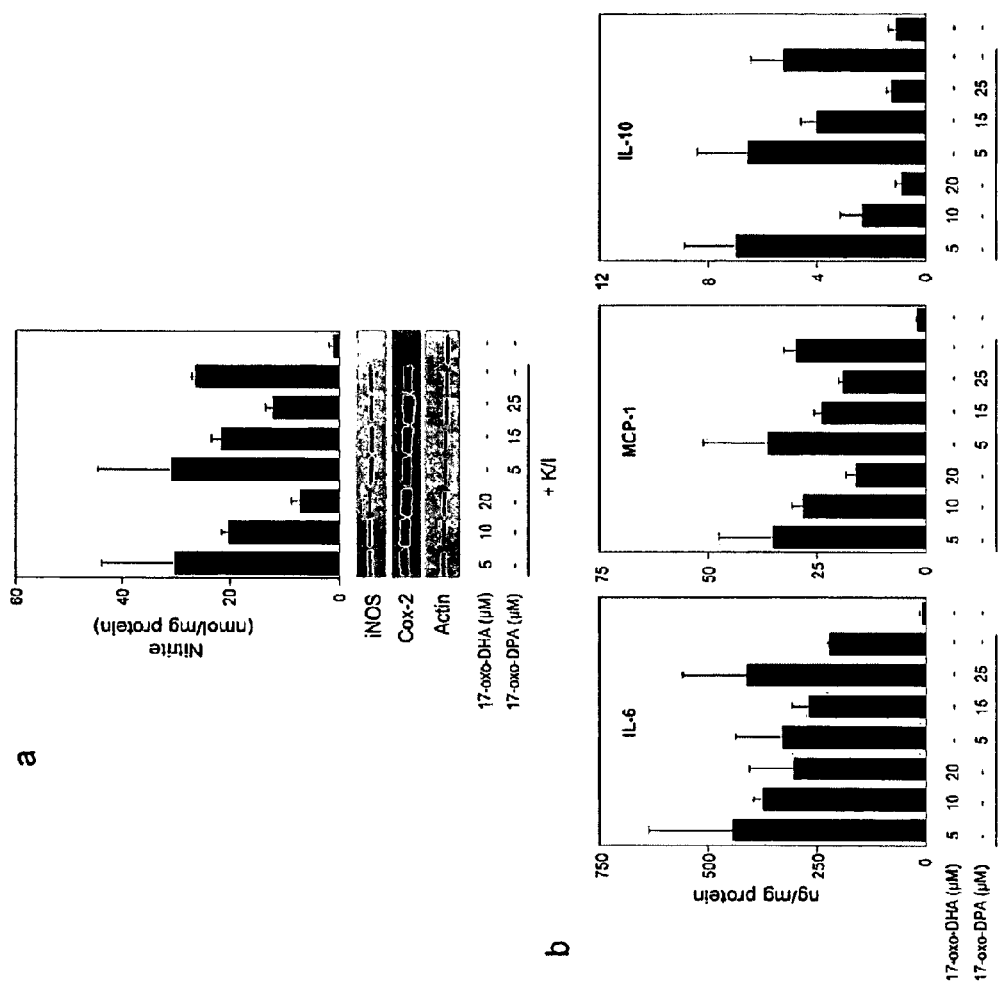
FIG. 24 illustrates that 17-oxoDHA and 7-oxoDPA modulate the inflammatory response in bone marrow-derived macrophages. Cells were treated with increasing concentration of 17-oxoDHA and 17oxoDPA for 6 h and $Kdo_2$ Lipid A (0.5 μg/ml) and IFNγ were added. Samples were collected at 12 h. (2) Nitrite levels were measured in the cell media and normalized to the total protein content: iNOS and COX-2 levels were measured in total cell lysates. (b) IL-6, MCP-1, and IL-10 levels were measured in cell media and normalized to the total protein content.

The intracellular levels of both MCP-1 and IL-10 were depressed in a dose-dependent manner following EFAD treatment. For example, ~80% reduction in the levels of MCP-1 was observed at the highest concentration of EFADs, while approximately 50% reduction was observed IL-6 (FIG. 11c). Similar results were observed in bone marrow-derived macrophage (BMDMs), (FIG. 23a). As shown in FIG. 11d, EFAD-1 and -2 strongly and dose-dependently repressed inducible nitric oxide synthase (iNOS) induction and subsequent accumulation of nitrite in the cell media both in RAW264.7 and in BMDMs (FIG. 23b).

In particular, a ~70% reduction of nitrite production was observed at 17-oxoDPA and 17-oxoDHA concentration of 25 and 20 μM respectively. Interestingly, Cox-2 induction was not affected by EFADs in this study. The expression of iNOS and the analyzed pro-inflammatory cytokines is dependent on the activity of NF-κB and Stat-1. It has been reported that electrophilic lipids can repress the activation of these transcriptional factors either by direct adduction to the DNA binding domain of the NF-κB subunit p65 and to the inhibitor IκBα or via indirect mechanisms. However, EFADs do not significantly inhibit p65 nuclear translocation and DNA binding or Stat1 phosphorylation.

The observation that oxo-fatty acids, such as 15d-PGJ$_2$[30], 5-oxoEPA, 6-oxoOTE, and the synthetic 4-oxoDHA[31], covalently bind and activate the peroxisome proliferator-activated receptor γ (PPARγ), prompted the present inventors to test the ability of 17-oxoDPA, and 17-oxoDHA to activate PPARγ. Thus PPARγ beta-lactamase reporter assays were performed using Roziglitazone, a potent synthetic PPARγ agonist, was used in the assay as positive control.

Both EFAd's (17-oxoDPA and 17-oxoDHA), activated PPARγ (FIG. 11e) with slightly higher EC$_{50}$s (~40 nM) as compared to the natural ligand 15d-PGJ$_2$ (~25 nM) and EC$_{50}$s that were orders of magnitude lower than 17-OH-DPA (>10 μM) and their corresponding native fatty acids (DHA and DPA).

Because, of their reactivity with biological thiols, the inventive EFAD's and their metabolites are believed to react with a cysteine, present in the binding pocket of the transcription factor of the COX-2 gene, and thereby inactivate the transcription factor. The result is an inhibition of inflammation by a lowering of cellular COX-2 levels.

The present invention also provides certain mimetics of Keto fatty acids or their metabolites whose synthesis is as described below.

Synthesis of the Mimetics of Keto Fatty Acid

The α,β-unsaturated ketone unit, found in a many bioactive molecules, is an important synthon in medicinal chemistry. Several syntheses have been reported for bioactive molecules involving the α,β-unsaturated ketone unit. See Synder, B. et al., *Org. Lett.*, (2001), 3(4), 569-572 and Bamford, S. et al., *Org. Lett.*, (2000), 2(8), 1157-1160.

Against this background, the inventors found that fatty acids according to Formula I are potent mediators of inflammatory response.

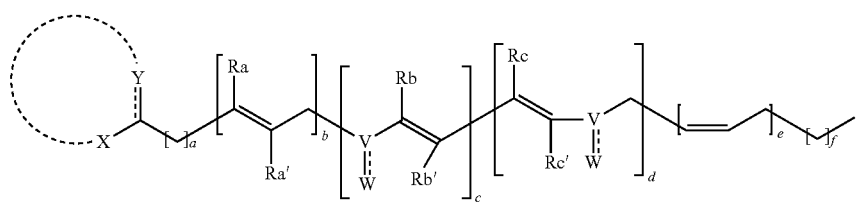

(I)

In particular, α,β-unsaturated keto fatty acids show a strong anti-inflammatory effect. Without endorsing any particular theory, the inventors believe that, in some embodiments, the keto and carboxylate groups of the unsaturated lipid contribute to electrostatic and hydrogen bonding interactions with residues that line the binding pocket of an effector protein.

The present invention, therefore, provides keto fatty acid mimetics that retain the above mentioned electrostatic and hydrogen bonding interactions. In some embodiments of the invention, mimetics that conform to Formula II below, are analogs of a heterocyclic dione conjugated to an α,β-unsaturated alkyl ketone. The dione functionality of the inventive mimetic is believed to occupy the same region within the effector protein's binding pocket as does the carboxylate head group of the lipid. Thus, the dione functionality would interact with the protein in the manner of the carboxylate group of a biological keto fatty acid. Moreover, by maintaining the position of the keto group in the tail region of the mimetic, compounds Formula (II) are believed to bind tightly to their targets.

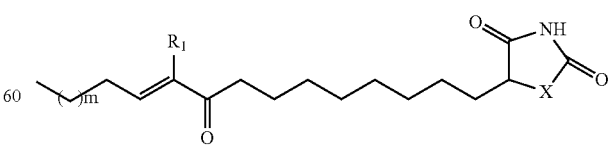

(II)

The synthesis of compounds shown in Formula II can be achieved by reacting an appropriately substituted nitrile with diethyl phosphonate, followed by a base catalyzed reaction of the enamine phosphonate with an aldehyde. Scheme 1 depicts this synthetic strategy.

Scheme 1:

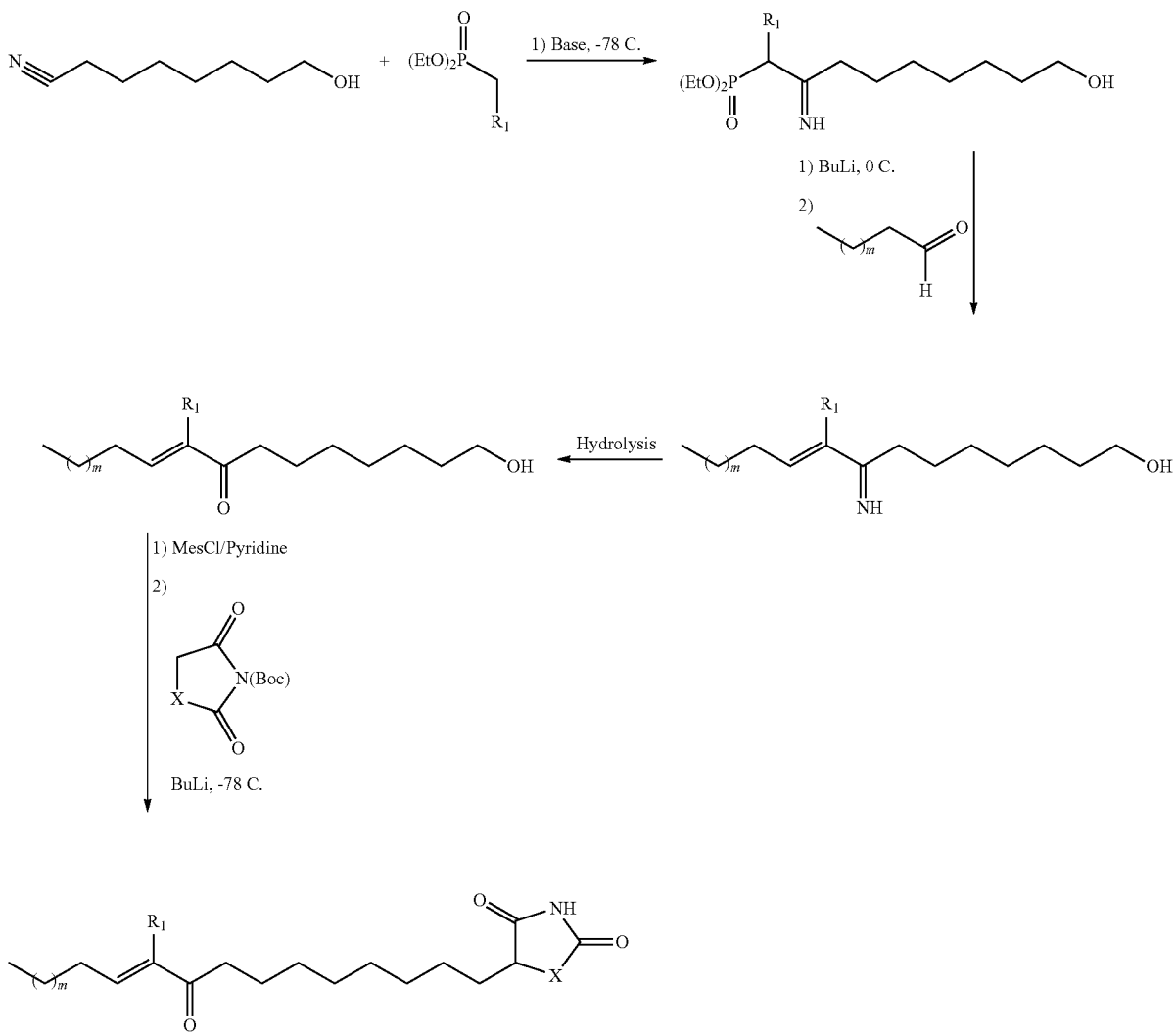

This strategy is versatile, allowing the conjugation of different heterocyclic diones to an appropriately functionalized α,β-unsaturated alkyl ketone. Thus, X in Scheme 1 can be a sulfur, oxygen or an unsubstituted or appropriately substituted nitrogen atom.

The strategy depicted in Scheme 1 also allows for the synthesis of mimetics that bear a substituent group on the carbon alpha to the keto group. Thus, $R_1$ in Scheme 1 is selected from the group consisting of hydrogen, $(C_1-C_8)$ alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

In a further embodiment, the inventive mimetic is a triazole derivative. See Formula III. Several studies indicate that the triazole unit is a mimic of a carboxylate group. Thus, putative mimetics incorporating a triazole unit in place of the carboxylate moiety are believed to bind in a manner similar to keto fatty acids to physiological targets implicated in anti-inflammatory activity. These compounds therefore are candidate therapeutics for treating inflammation.

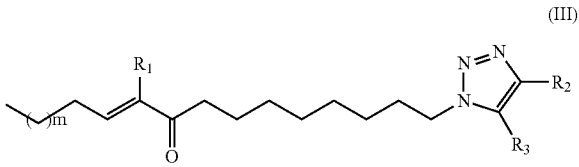

(III)

Compounds shown by Formula III can readily be synthesized using "click" chemistry. Thus, reaction of the azide of an α,β-unsaturated alkyl ketone with appropriately substituted alkynes in the presence of a catalyst results in the triazole mimetic. Scheme 2 illustrates the various synthetic steps that lead to the inventive triazole mimetics.

Scheme 2:

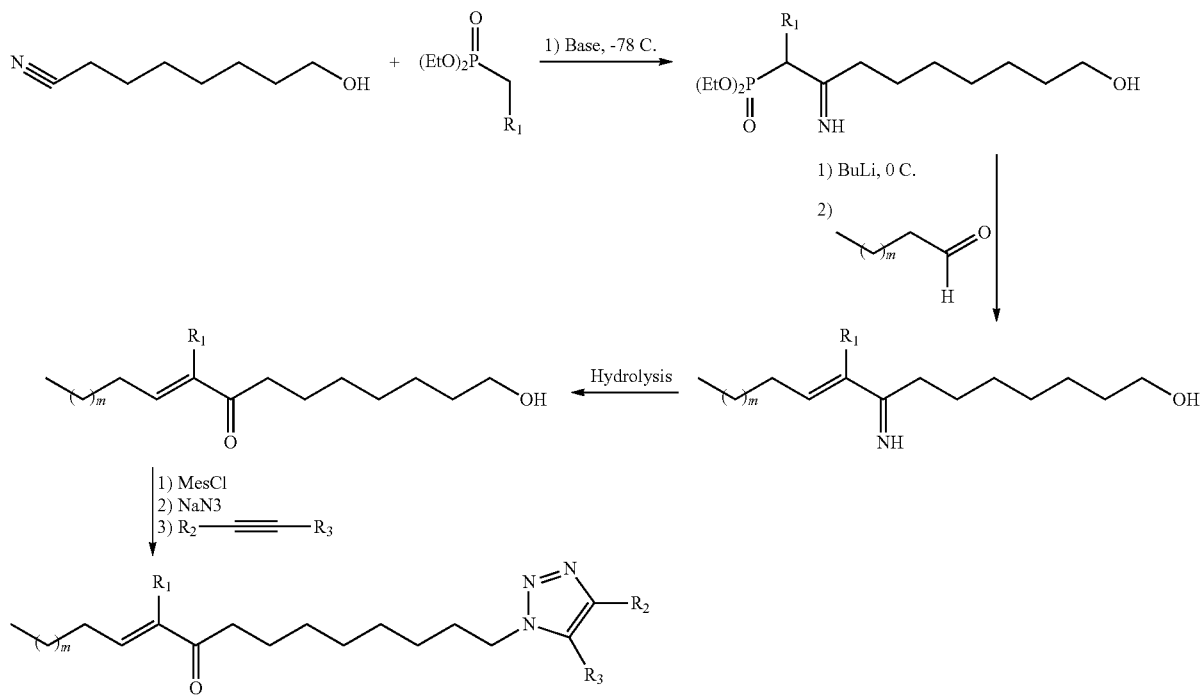

Thus, $R_1$, $R_2$ and $R_3$ in Scheme 2 are each independently selected from the group consisting of hydrogen, $(C_1$-$C_8)$ alkyl, $(C_2$-$C_8)$alkenyl, $(C_2$-$C_8)$alkynyl, $(C_1$-$C_4)$alkoxy, $(C_1$-$C_4)$alkoxy$(C_1$-$C_4)$alkyl, $(C_1$-$C_8)$fluoroalkyl, $(C_1$-$C_8)$hydroxyalkyl, $(C_3$-$C_8)$cycloalkyl, $(C_4$-$C_8)$bicycloalkyl, $(C_3$-$C_8)$ heterocycloalkyl, heteroaryl, aryl, $(C_3$-$C_8)$cycloalkyl$(C_1$-$C_6)$ alkyl, $(C_3$-$C_8)$heterocycloalkyl$(C_1$-$C_6)$alkyl, heteroaryl$(C_1$-$C_6)$alkyl and aryl$(C_1$-$C_6)$alkyl.

Formulations of Keto Fatty Acids, Metabolites and Mimetics

In accordance with one of its aspects, the present invention provides a formulation of a keto fatty acid, its metabolite or mimetic that comport with Formulae I-III, and their pharmaceutically acceptable salt, solvate or hydrate and a pharmaceutically acceptable carrier. Also contemplated are formulations having one or more therapeutic agents in addition to compounds of the invention. Non-limiting examples of therapeutics added to the inventive formulation include chemotherapeutic agents, antibodies, antivirals, steroidal and non-steroidal anti-inflammatories, conventional immunotherapeutic agents, cytokines, chemokines, and/or growth factors. In a further aspect, the inventive composition contains two or more of the Formulae I-III compounds described above, formulated together.

In a formulation of the invention, more than one physiologically acceptable carrier can be used, such as a mixture of two or more carriers. Additionally, an inventive formulation can include thickeners, diluents, solvents, buffers, preservatives, surface active agents, excipients, and the like.

The compounds of the invention can include pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of inventive compounds of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, beta.-hydroxybutyric, galactaric and galacturonic acids.

Suitable pharmaceutically acceptable base addition salts used in connection with the inventive compounds of the invention include metallic ion salts and organic ion salts. Exemplary metallic ion salts include, but are not limited to, appropriate alkali metal (group Ia) salts, alkaline earth metal (group Ia) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an inventive compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, Modern Pharmaceutics, Banker & Rhodes, Marcel Deldcer, Inc. (1979); and Goodman & Gilman's, The Pharmaceutical Basis of Therapeutics, 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

In other embodiments the inventive formulations are solid dosage forms for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

The solid dosage form can be a liquid or gelatin formulation prepared by combining the inventive compound with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an inventive compound prepared as described above may be lyophilized to for a solid that may be mixed with one or more pharmaceutically acceptable excipient, carrier or diluent to form a tablet, and in yet another embodiment, the inventive compound of an oily preparation may be crystallized to from a solid which may be combined with a pharmaceutically acceptable excipient, carrier or diluent to form a tablet.

Further embodiments which may be useful for oral administration of inventive compounds include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, inventive compounds of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids has between about twelve carbons to about eighteen carbons. In some embodiments, the amount of ethoxylation can vary from about 2 to about 200, about 5 to 100, about 1.degree. to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from C J Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, Handbook of Pharmaceutical Excipients, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, macrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, Handbook of Pharmaceutical Excipients, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulamm C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™. BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH$_2$-CH$_2$-. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to sorbitols such as PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, Handbook of Pharmaceutical Excipients, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include inventive compounds administered in combination with other active such as, for example, adjuvants, protease inhibitors, or other compatible drugs or compounds where such combination is seen to be desirable or advantageous in achieving the desired effects of the methods described herein.

Route of Administration

The inventive compounds of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an inventive compound may be deposited to a site of injury or inflammation, such as, for example, the site of a surgical incision or a site of inflammation due to arthroscopy, angioplasty, stent placement, by-pass surgery and so on.

In certain other embodiments, the compounds of the invention may be applied locally as a salve or lotion applied directly to an area of inflammation. For example, in some embodiments, a lotion or salve including inventive compounds of the invention may be prepared and applied to a burn, radiation burn, site of dermal disorder, edema, arthritic joint or the like.

Various embodiments, of the invention are also directed to method for administering inventive compounds. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties.

In various embodiments, an effective amount of an inventive compound delivered during each administration cycle may range from about 10 mg/m.sup.2/day to about 1000 mg/m$^2$/day. In some embodiments, an effective amount may be about 20 mg/m$^2$/day to about 700 mg/m$^2$/day, and in others, an effective amount may be about 30 mg/m$^2$/day to about 600 mg/m$^2$/day. In particular embodiments, an effective amount may be about 50 mg/m$^2$/day, about 400 mg/m$^2$/day, about 500 mg/m$^2$/day, or about 600 mg/m$^2$/day. In yet other embodiments, an effective amount of an inventive compound may vary as treatment progresses. For example, a dosage regimen may be increased or decreased as treatment proceeds through administration cycles, or the daily dosage may increase or decrease throughout administration. In additional embodiments, greater than 1000 mg/m$^2$/day may be administered because even high doses of inventive compound are generally tolerable to the patient and may not produce undesired physiological effects.

The pharmaceutical carrier used to formulate the inventive compounds will depend on the route of administration. Administration may be topical (including opthamalic, vaginal, rectal, or intranasal), oral, by inhalation, or parenterally, for example by intravenous drip, subcutaneous, intraperitoneal or intramuscular injection.

Thus, the compounds of the invention can be administered intravenously, intraperitoneally, intramuscularly, subcutaneously, intracavity, transdermally, intratracheally, extracorporeally, or topically (e.g., topical intranasal administration or administration by inhalant). In this regard, the phrase "topical intranasal administration" connotes delivery of the compositions into the nose and nasal passages through one or both of the nares and can comprise delivery by a spraying mechanism or droplet mechanism, or through aerosolization of the nucleic acid or vector. The latter can be effective when a large number of subjects are to be treated simultaneously. Administration of the compositions by inhalant can be through the nose or mouth via delivery by a spray or droplet mechanism. Delivery can also be directed to any area of the respiratory system (e.g., lungs) via intubation.

Formulations of the inventive keto fatty acid mimetics for parenteral administration will include excipients and carriers that stabilize the nitro fatty acid mimetic. Illustrative of such a carrier are non-aqueous solvents, such as propylene glycol, polyethylene glycol, vegetable oils, and injectable organic esters such as ethyl oleate. Additionally, formulations for parenteral administration include liquid solutions, suspensions, or solid forms suitable for solution or suspension in liquid prior to injection, or emulsions.

Intravenous formulations of the mimetics include agents to maintain the osmomolarity of the formulation. Examples of such agents include sodium chloride solution, Ringer's dextrose, dextrose, lactated Ringer's solution, fluid and nutrient replenishers, and the like. Also included in intravenous formulations are one or more additional ingredients that prevent microbial infection or inflammation, as well as anesthetics.

The present invention also provides formulations of the pharmaceutically acceptable salts of the inventive mimetics. Illustrative of such salts are those formed by reaction of the mimetics with an inorganic base such as sodium hydroxide, ammonium hydroxide, or potassium hydroxide. Also contemplated are salts of the inventive mimetics with organic bases such as mono-, di-, trialkyl and aryl amines and substituted ethanolamines.

In yet another aspect, a mimetic of the invention can be formulated as a prodrug. At physiological pH, a mimetic of a keto fatty acid typically will be a charged molecule, which may have non-optimal bioavailability and cell-transport kinetics. To address these concerns, therefore, one may provide a compound of the invention as a pharmaceutically acceptable ester, such as a methyl or an ethyl ester. The ester acts as a prodrug because non-specific intracellular esterase convert it in vivo to the active form.

Methods of Treatment

Compounds in accordance with the present invention may be administered to individuals to treat, ameliorate and/or prevent a number both acute and chronic inflammatory and metabolic conditions. In particular compounds in accordance with Formulae I-III as well as their metabolites may be used to treat acute conditions including general inflammation, autoimmune disease, autoinflammatory disease, arterial stenosis, organ transplant rejection and burns, and chronic conditions such as, chronic lung injury and respiratory distress, diabetes, hypertension, obesity, arthritis, neurodegenerative disorders and various skin disorders. However, in other embodiments, inventive compounds may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

When administered inventive compounds may interact with a number of cellular receptors and/or proteins that mediate inflammation, either by inhibiting or stimulating their activity thereby inhibiting or reducing inflammation. Without wishing to be bound by theory, the inventors believe that inventive compounds can modulate important signaling activities including, for example, neurotransmission, gene expression, vascular function and inflammatory responses. Chemical properties of inventive compounds that may facilitate these activities include, but are not limited to, the strong, reversible electrophilic nature of the β-carbon adjacent to the electron withdrawing vinyl group, an ability to undergo Nef-like acid base reactions to release NO, an ability to partition into both hydrophobic and hydrophilic compartments, and a strong affinity for G-protein coupled receptors and nuclear receptors.

For example, in one embodiment, the inventive compounds may be administered to mediate cell signaling via multiple G-protein coupled receptors and nuclear receptors such as, but not limited to, peroxisome proliferator-activated receptors (PPAR) including PPAR.alpha., PPAR.gamma., and PPAR.delta. PPAR is a nuclear receptor that is expressed throughout an organism, including in monocytes/macrophages, neutrophils, endothelial cells, adipocytes, epithelial cells, hepatocytes, mesangial cells, vascular smooth muscle cells, neuronal cells and when "activated" induces transcription of a number of target genes. Activation of PPAR has been shown to play various roles in regulating tissue homeostasis including, for example, increasing insulin sensitivity, suppress chronic inflammatory processes, reduce circulating free fatty acid levels, correct endothelial dysfunction, reduce fatty streak formation, delay plaque formation, limit blood vessel wall thickening and enhance plaque stabilization and regression. The inventive compounds embodied herein may perform each of these functions associated with PPAR activation.

Moreover, inventive compounds may perform these functions without significantly altering normal cellular process. For example, in one embodiment, an inventive compound may be administered to treat hypertension by lowering blood pressure to normal levels without reducing the blood pressure of the individual below normal levels even if the inventive compound is over-administered. Thus, without wishing to be bound by theory, the compounds of the invention may provide treatment of an individual without the negative affects associated with over-administration or over-treatment using traditional medications.

EXAMPLES

Experimental Methods

Materials

Diclofenac, methyl arachidonyl fluorophosphonate, MK886, (±)-Ibuprofen, Indomethacin, NS-398, 15d-PGJ$_2$, 4-hydroxy-2-nonenal, 9-OxoODE, 5-OxoETEd7, 12-Oxo-ETE, 15-OxoEDE, 9-OxoOTrE, 17-OxoDPA, and 17-OxoDHA were purchased from Cayman Chemicals (Ann Arbor, Mich.). Ovine placental COX-2 (Cayman 60120) was also from Cayman Chemicals. DPA and DHA were from NuCheck Prep (Elysian, Minn.). Kdo$_2$ lipid A was from Avanti Polar Lipids, Inc (Alabaster, Ala.). HPLC solvents were from Honeywell Burdick and Jackson (USA). Glutathione and glutathione S-transferase were purchased from Sigma-Aldrich.

Cell Culture and Treatment

Murine monocyte/macrophage cells (RAW264.7) and human monocyte cells (THP-1) were obtained from ATCC (USA) and maintained at 37° C. in 5% CO$_2$ in DMEM+10% FBS (RAW264.7) and RPMI+10% FBS (THP-1) according to ATCC guidelines. L-cells were obtained from ATCC(CCL-1) and maintained at 37° C. in 5% CO$_2$ in DMEM supplemented with 10% FBS, glutamine (2 mM), sodium pyruvate (1 mM), penicillin, streptomyocin and non-essential amino acids.

For activation experiments RAW 264.7 cells were seeded, incubated overnight, and treated at approximately 80% confluence with the indicated compounds[47]. Non-activated controls were treated with vehicle alone. During activation, cells were maintained in an activation medium (SMEM) of Minimum Essential Medium Eagle (Cellgro, 17-305)+2% FBS supplemented with L-glutamine (584 mg/L), Na-pyruvate (110 mg/L) and Hepes (3.57 g/L, pH 7.4). For inhibition studies, inhibitors were added to the medium at the time of activation and MIT assays were used to confirm cell viability. Cells were harvested 20 h post activation (unless otherwise indicated) in 50 mM phosphate buffer (pH 7.4) and snap frozen in liquid N$_2$. THP-1 cells were differentiated with PMA (86 nM) for 16 h, activated with IFNγ (200 U/ml) and Kdo$_2$ lipid A (0.5 μg/ml) in RPMI+2% FBS and harvested 40 h after differentiation. For treatment with EFADs alone, 17-oxoDHA and 17-oxoDPA were added to cell culture media at the indicated concentrations and for the indicated time period. For treatment with EFADs coupled with pro-inflammatory stimulation, addition of 17-oxoDHA and 17-oxoDPA was followed by addition of Kdo$_2$ and IFNγ at 6 h.

Trans-Alkylation Reaction of Electrophiles with BME.

Upon thawing, lysates were exposed to BME (500 mM+internal standard, 5-OxoETEd7 (1.25 ng/ml)) and incubated at 37° C. for 1 h in 50 mM phosphate buffer (pH=7.4) as previously described[22]. Proteins were precipitated with cold acetonitrile and the supernatant was analyzed by HPLC-ESI-MS/MS.

HPLC-ESI-MS/MS

Samples were separated by reverse-phase HPLC using a 20×2 mm C18 Mercury MS column (3 μm, Phenomenex). A gradient solvent system was used consisting of A (water/0.1% formic acid) and B (acetonitrile/0.1% formic acid) at 750 μl/min under the following conditions: hold at 35% B for 0.5 min, then 35-90% B in 4 min, 90-100% B in 0.1 min, hold for 1.4 min and 100-35% B for 0.1 min, hold for 1.9 min. To achieve resolution of isomers, chromatographic runs were performed using a 150×2 mm C18 Luna column (3 μm, Phenomenex). A flow rate of 250 μl/min was used under the following conditions: hold at 35% B for 3 min, then 35-90% B for 23 min, then 90-100% B in 0.1 min, hold for 5.9 min and 100-35% B for 0.1 min, hold for 7.9 min. The analysis and quantification of BME adducts were performed using a hybrid triple quadrupole-linear ion trap mass spectrometer (4000 Q trap, Applied Biosystems/MDS Sciex) in the neutral loss (NL) scan mode, multiple reaction monitoring (MRM) scan mode, and the enhanced product ion analysis (EPI) mode. The following settings were used: declustering potential −90 and −50 V, and collision energy −30 and −17 V for free fatty acids and BME adducts, respectively. Zero grade air was used as source gas, and N$_2$ was used in the collision chamber. EFADs were quantified using external synthetic standards, when available, and by comparing peak area ratios between analytes and a 5-OxoETEd7 internal standard. Data were acquired and analyzed using Analyst 1.4.2 software (Applied Biosystems, Framingham, Mass.).

COX-2 Reactions

Ovine placental COX-2 (20 U/ml) was preincubated in Tris/heme/phenol (THP) buffer±2 mM ASA at 37° C. THP buffer, freshly prepared before each reaction, consisted of Tris•Cl (100 mM, pH 8.1), hematin (1 μM), and phenol (1 μM). The reaction was initiated by addition of the indicated fatty acids at a concentration of 10 μM. Reactions were terminated at the indicated time points by addition of ice-cold acetonitrile (9× reaction volume) and COX-2 protein was removed by centrifugation. Product formation was monitored by RP-HPLC-MS/MS in multiple reaction monitoring (MRM) mode following the loss of CO$_2$ (m/z 345/301 and m/z 343/299 for OH-DPA and OH-DHA, respectively).

Preparation of Primary Macrophages

Bone marrow derived macrophages were isolated from C57BL/6 mice according to the protocol developed by Davies. See Davies, J. Q. & Gordon, S. Isolation and culture of murine macrophages. *Methods Mol Biol* 290, 91-103 (2005).

Western Blot

Protein concentrations of samples were measured by BCA assay (Pierce). The following primary antibodies were used: Nrf2 (Santa Cruz, sc-722), HO-1 (Assay Design, SPA-896), Nqo1 (Abcam, ab34173), Cox-2 (Santa Cruz, sc-1745), iNOS (BD Transduction Lab, 610332), Lamin B1 (Abcam, ab16048). Actin (detected by Sigma A2066) was used as loading control. Secondary antibodies were purchased from Santa Cruz Biotechnology.

Nitrate/Nitrite Measurement

Total nitrite and nitrate concentration was measured in cell culture media by Griess reaction using the Nitrate/Nitrite Colorimetric Assay Kit (Cayman Chemical).

Measurement of Glutathione Adducts

GS-adducts were analyzed in cell pellets and media by nano-LC-MS/MS using nanoACQUITY UltraPerformance LC coupled with Thermo-Fisher LTQ. GS-5-oxoETE-d7 was added as internal standard. Waters XBridge BEH130 C18 NanoEase Column (3.5 μm, 100 μm×100 mm) was used. Chromatography was performed using a binary flow system consisting of A (H$_2$O/0.1% formic acid) and B (acetonitrile/ 0.1% formic acid) at 0.5 μl/min under the following conditions: hold at 1.5% B for 3 min, then 1.5 to 30% B in 10 min, then 30 to 70% B in 27 min. The following parent ions were monitored for identification of, respectively, GS-5-oxoETE-d7, GS-oxoDHA and GS-oxoDPA: 633.3, 650.3 and 652.3.

Statistics.

Data are expressed as mean±SD and were evaluated by a one-way analysis of variance, post-hoc Tukey's test for multiple pairwise comparisons. Significance was determined as $p<0.01$ unless otherwise indicated.

Reactive Electrophilic Species (RES)

RES are molecules characterized by having an electron-withdrawing functional group that renders the α-carbon electron-poor and reactive towards electron-rich donor molecules (nucleophiles). The strength of the electron withdrawing group will determine the reactivity of the electrophile. Two prominent examples of these electron withdrawing groups are α,β-unsaturated carbonyls and nitroalkenes, in which the β-carbon (if it is bound to at least one hydrogen atom) is the site of nucleophilic attack. The resonance structure of electrophiles like these allows them to react covalently with many nucleophiles via Michael addition. Interestingly, the reactivity of the electrophilic compound appears to directly relate to the biological outcome of each electrophile[13] with irreversible adducts conveying toxic effects[14]. In addition, RES also modulate the cell redox potential by changing the GSH/GSSG redox couple, which can further impact underlying cell signaling. By covalently modifying proteins, RES can initiate cell signaling events and modulate enzymatic activity and subcellular localization[15]. RES production and levels are tightly controlled in healthy cells with low levels of these species inducing the expression of cell survival genes, and in some cases priming the cells to survive periods of stress. In contrast, under pathological conditions, RES are often produced in excess and overcome signaling events and protective pathways, accelerating cell damage[16]. Recently, there has been a move towards employing RES in the prevention or treatment of various diseases such as neurodegeneration, cancer, and other pathologies presenting a significant inflammatory component. For example, electrophilic neurite outgrowth-promoting prostaglandin compounds display protective effects during cerebral ischemia/reperfusion, which are attributed to their accumulation in neurons and subsequent activation of the Keap1/Nrf2 pathway[17]. Other RES (e.g. avicins[18] and Bis(2-hydroxybenzylidene)acetone[19], isothiocyanates[20]) are potential chemopreventative agents, due to their abilities to induce apoptosis of precancerous cells and tumor cells. Additionally, the electrophile 15d-PGJ$_2$ demonstrates a protective role in animal models of acute lung injury[21].

EFADs are Produced by Primary Macrophages Isolated from Mouse Bone Marrow

Figure 8:
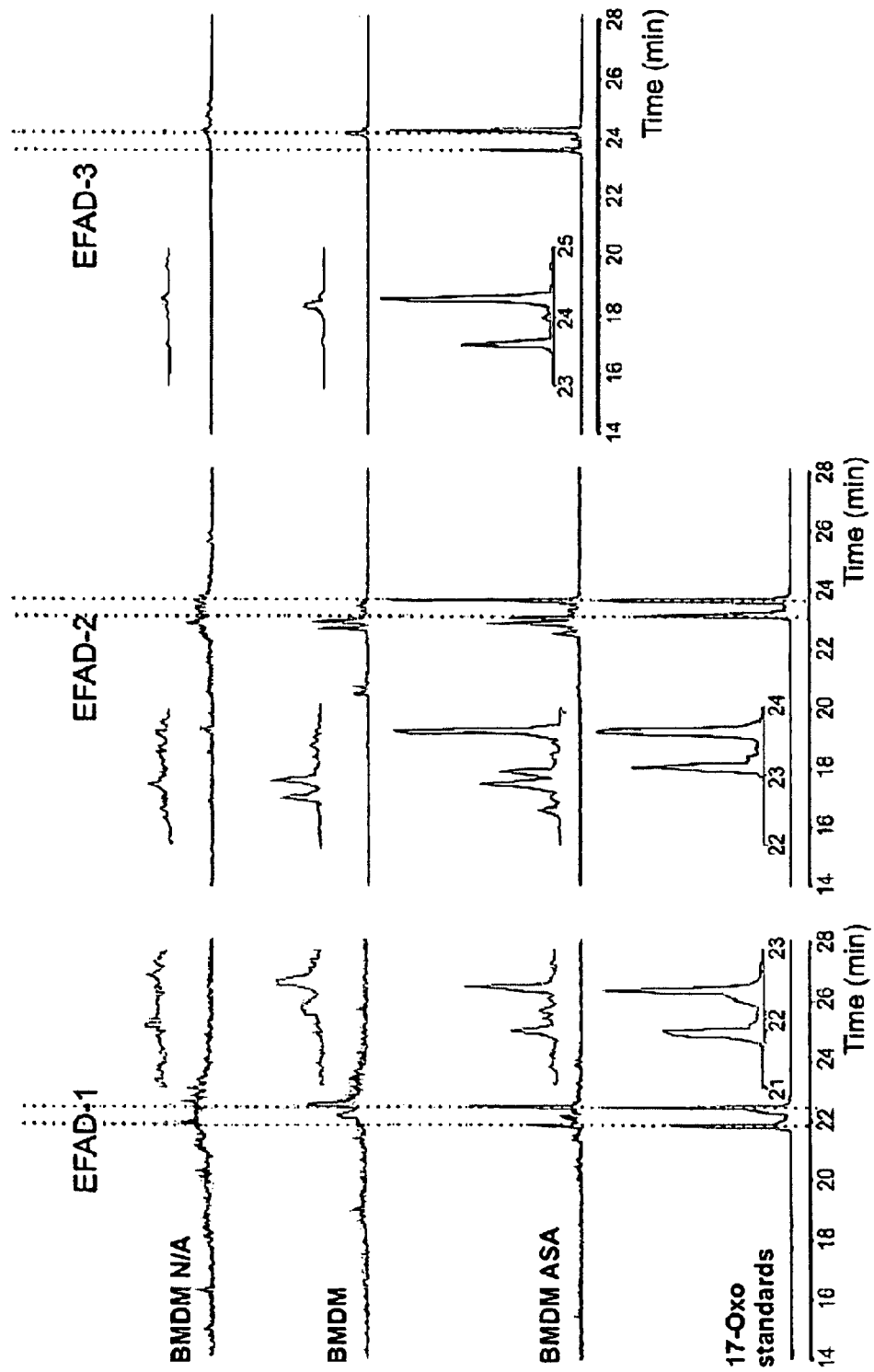
FIG. 8 illustrates formation of EFAD in activated primary murine macrophages. Bone marrow derived macrophages were activated with $Kdo_2$ (0.5 μg/ml) and IFNγ (200 U/ml) and EFADs were detected 10 h post activation.

Since RAW 264.7 cells (and potentially other macrophage cell lines) have an altered AA metabolism[26], it was important to demonstrate that the formation of EFADs occurred in primary cell lines as well. Thus, C57BL/6 murine primary hematopoietic stem cells were differentiated to macrophages, activated with Kdo$_2$ and IFNγ/and analyzed for the formation of EFADs. Five out of the six EFAD species (EFAD-1, 2, -3, -5 and -6) were observed which co-eluted with those produced by RAW 264.7 cells and with the available standards. Similar to what was observed in RAW264.7 cells, when activated bone marrow-derived macrophage (BMDM) cells were treated with ASA the extent of EFAD formation was increased about two to three fold and in the case of EFAD-1 and -2, the isomeric composition shifted from 13-oxo to 17-oxo species (FIG. 8).

Kinetics and Identification of EFADs Adduct to Proteins and Glutathione (GSH)

Figure 9:
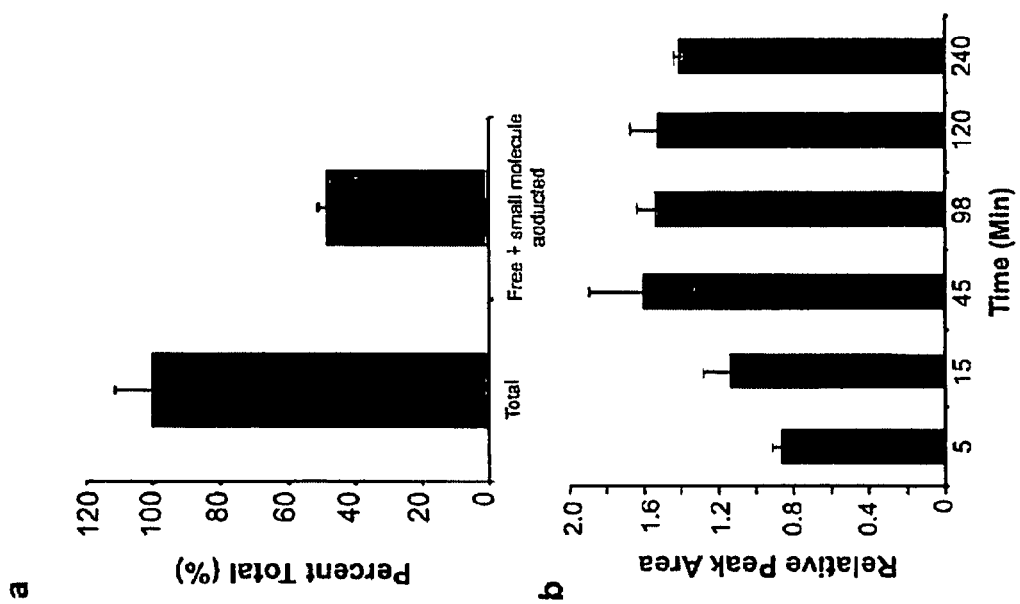
FIG. 9 shows the formation of EFAD adducts with proteins in the cell. (a) RAW264.7 cells were activated with $Kdo_2$ (0.5 μg/ml) and IFNγ (200 U/ml) and harvested 20 h post activation. Cell lysates were then split into two groups (and internal standard was added): treatment with 500 mM BME followed by protein precipitation with acetonitrile ("Total") and protein precipitation with acetonitrile followed by treatment with 500 mM BME ("Free+small molecule adducted"). EFAD-2 levels were quantified by RP-HPLC-MS/MS. (b) Time-course reaction of EFAD-2 with BME in RAW264.7 activated cell lysates.

Biological electrophiles, such as EFAD's react with sulfhydryl groups of proteins as well as the cellular reductant GSH[15,27-29]. Different approaches have been used to demonstrate the occurrence and extent of adduct formation by EFAD's to proteins and small molecule sulfhydryls. To demonstrate the occurrence of sulfhydryl adducts in activated cells, total EFAD content was quantified and compared with the pool of free EFADs (including EFADs adducted to small molecules such as glutathione). The difference between the two groups gave the percentage of EFADs adducted to proteins (~51%) (FIG. 9a). To confirm the distribution of intracellular EFADs, between free and adduct form both free and adducted EFAd's were allowed to react with BME. The difference in reaction kinetics of free EFAD with BME and adducted EFAD with BME was used to confirm the distribution of intracellular EFADs, between free and adduct form.

Figure 20:
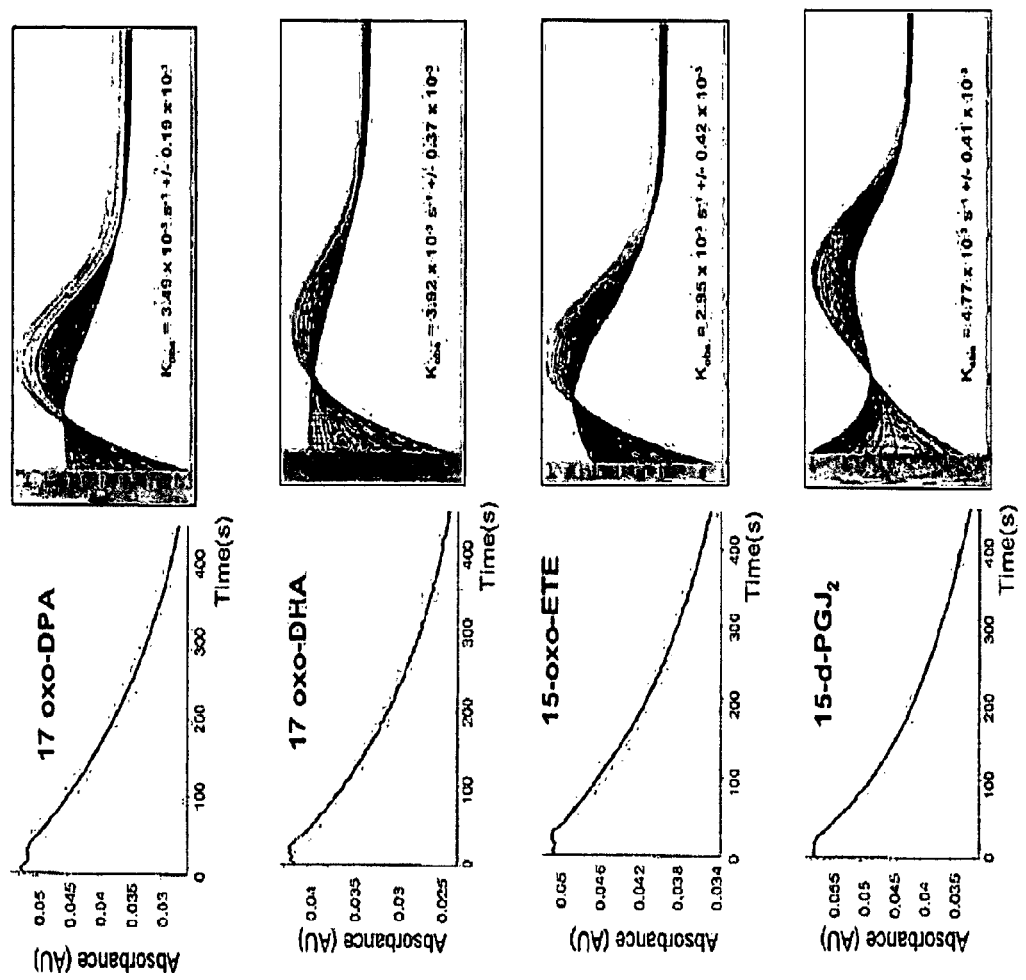
FIG. 20 illustrates that EFADs have a similar reactivity towards BME compared to other α,β-unsaturated keto fatt-acid. The pseudo first order reaction rates of various BME (50 mM) and α,β-unsaturated keto fatty acids (2.9 μM) were measured spectrophotometrically using a Agilent 8453 diode array. The absorbance changes (decrease) were followed at 309 nm (15d-$PGJ_2$), 289 nm (17-oxo-DHA and 17-oxo-DPA) and 287 nm (15-oxoETE) (left panel). The reaction was carried out in phosphate buffer pH 7.4 at 37° and 450 spectras were recorded (at 1 spectrum per sec) as shown in panels on the right. The decrease in absorbance was adjusted to a first order-curve using UV-Vis ChemStation (Agilent).
Figure 21A:
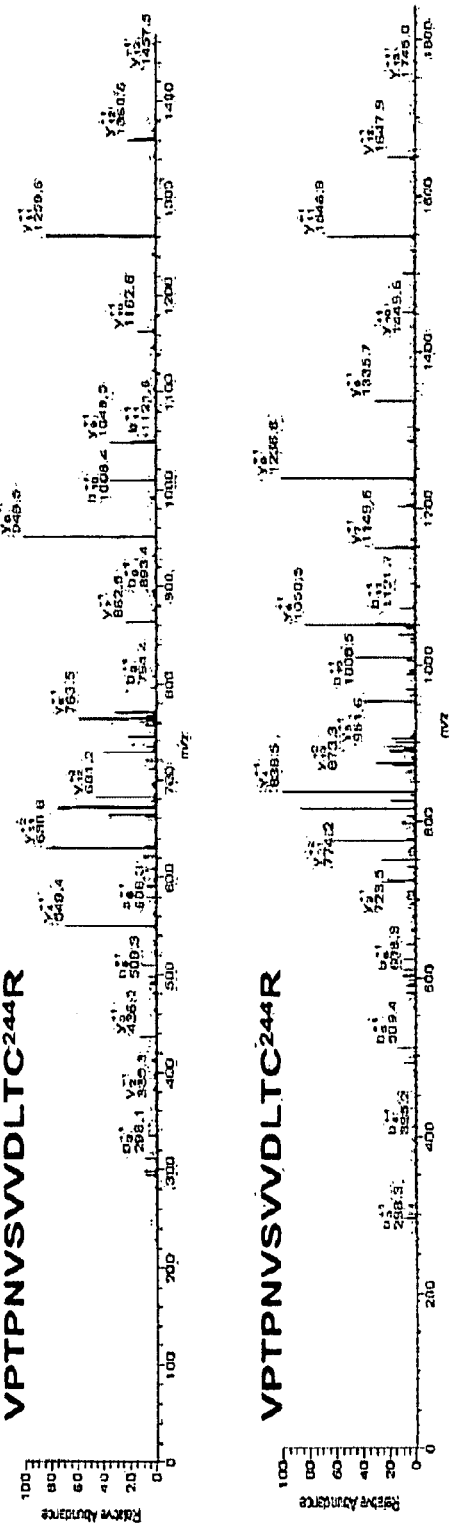
FIG. 21 illustrates the mass spectrometric analysis of an in vitro reaction of GAPDH vith EFAD-2. Four residues were detected and confined—as being targets for EfAD-2 in treated rabbit GAPDH. The peptides were alkylated as Cys244 (a), His163 (b), Cys149 (c) and His328 (d). Upper panels show EFAD-2 modified peptides and lower panels show spectra from corresponding native peptide.
Figure 21B:
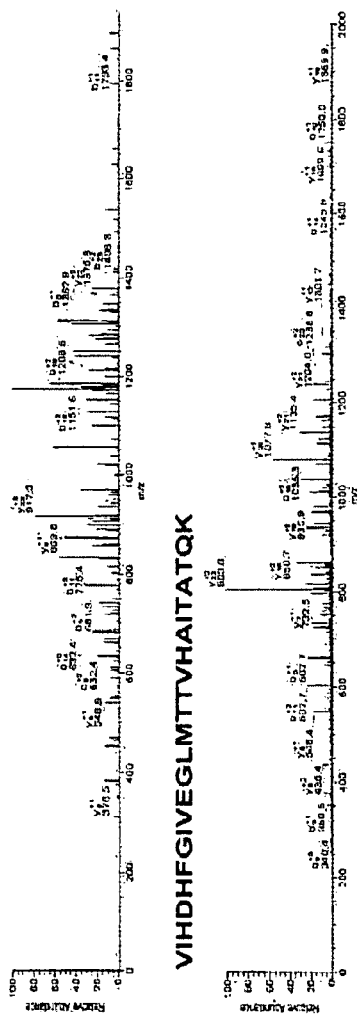
Figure 21C:
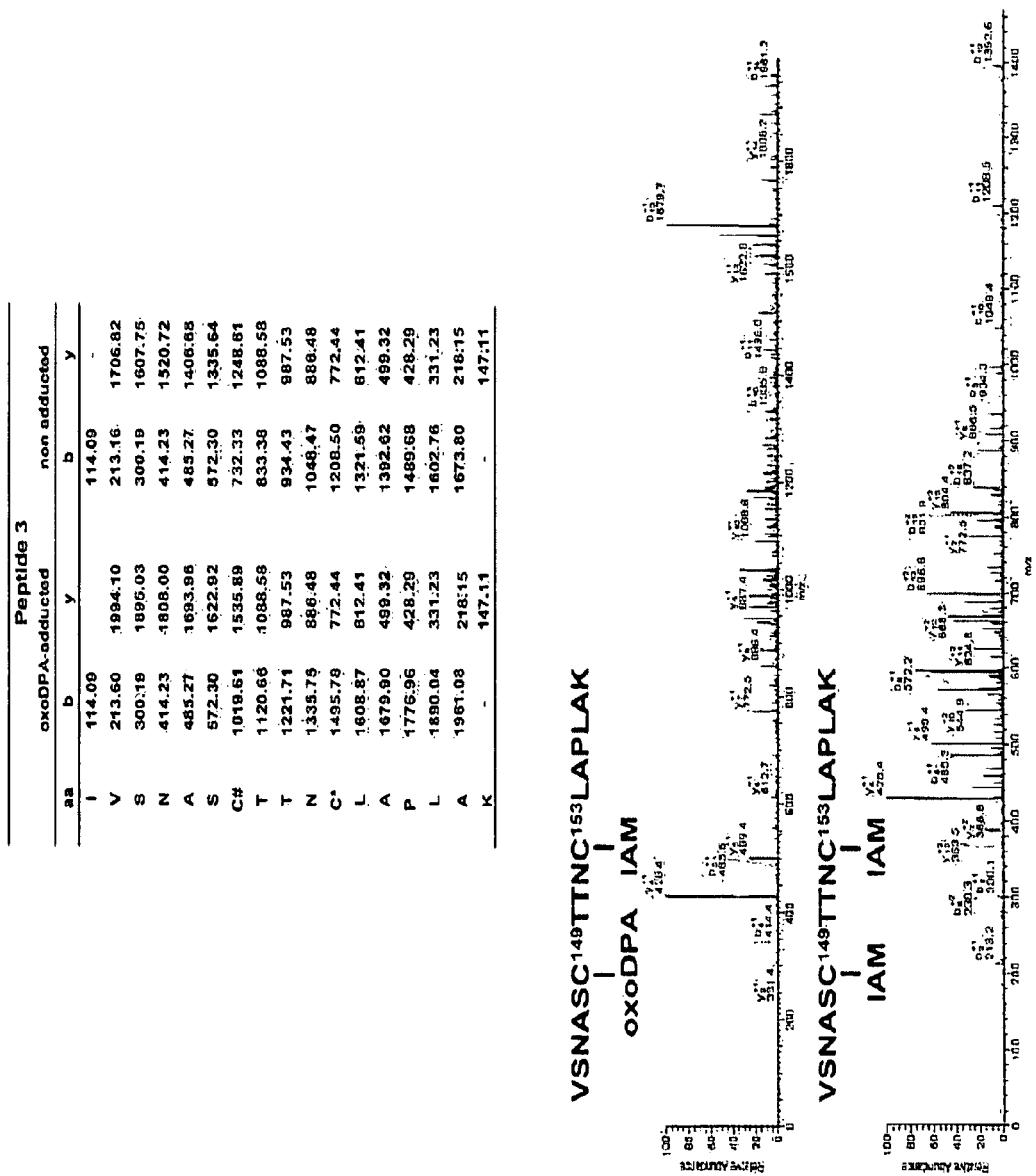
Figure 21D:
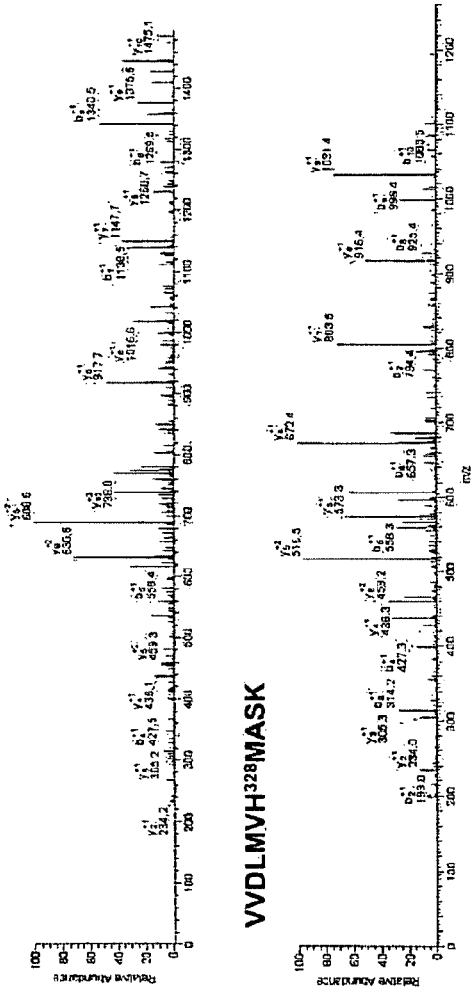

Typically, reaction rates of BME with free electrophiles is fast with a calculated pseudo first order reaction rate constant in the range of about $3\times10^{-3}$ and $5\times10^{-3}$ sec$^{-1}$ for the different α,β-unsaturated oxo-fatty acids tested (15d-PGJ$_2$, EFAD-1, EFAD-2) (FIG. 20). In contrast, reactions rates with adducted electrophiles are slower, depending on the rate constant ($k_{off}$), for the Cys-EFAD and His-EFAD adducts. The time-dependent characteristic of these reactions was used to further confirm the adducted populations present in the cell lysates (FIG. 9b).

Fast kinetics with free EFADs and a slower t reaction rate for the displacement of EFADs from adducted proteins were observed. Approximately 50% of the EFADs reacted with BME within the first 5 min, suggesting that protein-adducted EFADs accounted for the remaining ~50% of total EFADs that reacted with BME after 45 min (FIG. 9b).

To more specifically test the binding of EFADs to nucleophilic residues in proteins, we tested whether GAPDH was alkylated by EFADs. This enzyme is a well-characterized target for electrophiles and becomes easily inactivated by nitrosylation, oxidation or nucleophilic addition. As expected and based on its electrophilic properties, the EFAD-2 synthetic standard (17-oxo-isoform) readily formed adducts with Cys244, Cys149, His163 and His328 residues of GAPDH in vitro (FIG. 21).

The cellular reductant glutathione reacts readily with biological electrophiles, such as EFAd's, via the sulfhydryl group of cysteine to give the corresponding glutathione-EFAD (GS-EFAD), adduct. The present inventors investigated whether EFADs were substrates for glutathione S-transferase (GST) and if GS-EFADs adducts were actually formed in cells during macrophage activation.

Figure 22:
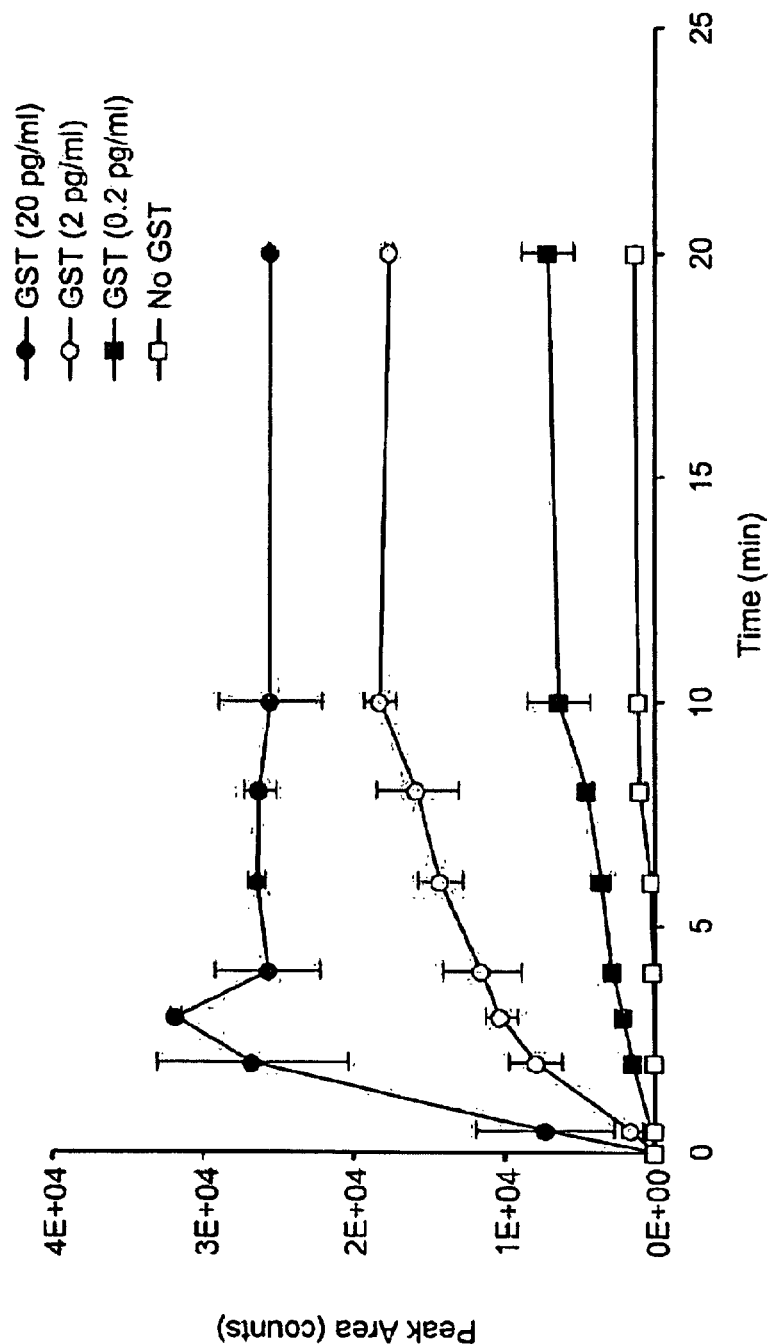
FIG. 22 illustrates that incubation of EFADs without or with increasing concentrations of glutathione transferase (GST), resulted in adduction rates that were dependent on the amount of added enzyme confirming that EFADs were substrate for GSTs.

Thus, incubation of EFADs without or with increasing concentrations of GST resulted in adduction rates that were dependent on the amount of added enzyme confirming that EFADs were substrate for GSTs (FIG. 22).

Figure 10:
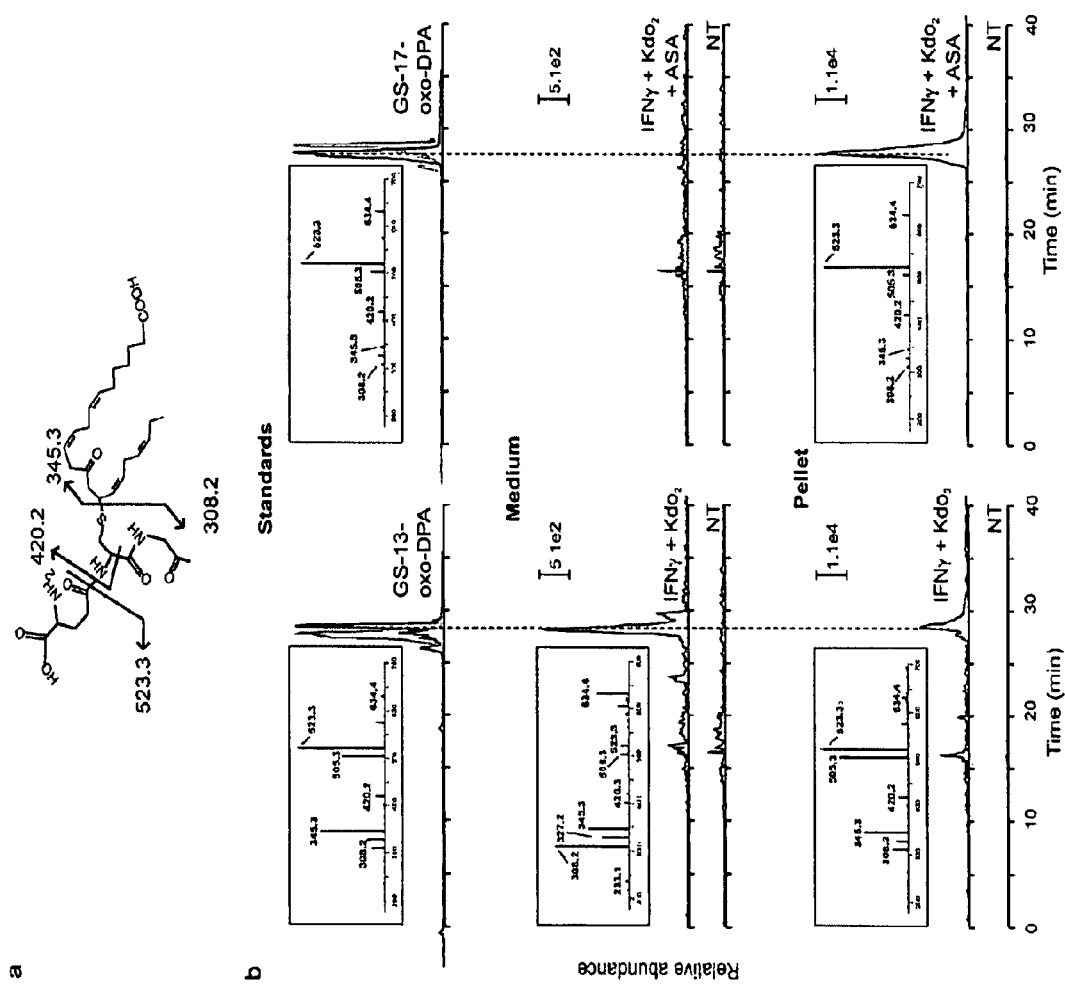
FIG. 10 illustrates detection of intracellular and extracellular GS-oxo-DPA adducts following activation of RAW264.7 cells. (a) Chemical structure and fragmentation pattern of GS-13-oxoDPA. (b) Chromatographic profiles and mass spectra of 13- and 17-oxoDPA derived from synthesized standards (upper panels), cell medium (middle panel) and cell pellet (lower panel). Differences due to recovery efficiency were taken into account by correcting the signal levels using the internal standard GS-5-oxoETE-d7. Fragments 345.3 and 523.3 were selected and monitored as the ones giving the best signal to noise ratio in samples derived from cell media and cell pellets, respectively. Fragment 634.4 derived from loss of $H_2O$ from the parent ion 652.4; m/z 523.3 and m/z 420.3 corresponded to fragments y2 and c1 typical of peptide fragmentation while 345.3 and 308.2 derived from the lipid and the glutathione molecule. m/z 505.3 and m/z 327.2 derived from loss of $H_2O$ from 523.3 and 345.3, respectively. K/I, cells treated with $Kdo_2$ and IFNγ, K/I+ASA, cells treated with $Kdo_2$, IFNγ and ASA; NT, non-treated cells.

FIGS. 10a, 10b and 22 illustrates results of a mass spectral analysis of glutathione adducts from cell lysates, cell medium of activated RAW264.7 cells, and compares these mass spectrums to the mass spectrum obtained from a reaction mixtures of a synthetically prepared GS-oxoDHA and GS-oxoDPA standard. The fragmentation patterns and retention times observed for GSH adducts of EFAD-1 and -2 corresponded to those obtained using the synthetic standards. Moreover, the addition of ASA enhanced the formation of GS-adducts, consistent with the concomitant increase in EFAD synthesis. GS-adducts were also found in the extracellular media, the only exception being that for samples treated with ASA, detection of GS-adducts in the extracellular media was unexpectedly reduced.

Discussion

Despite current knowledge on a wide range of lipid signaling mediators, the question as posed by Harkewicz et al. still remains: "are biologically significant eicosanoids [or other fatty acid-derived metabolites] being overlooked?" Herein we address this question by focusing the search for negatively charged lipid metabolites on those with reversible electrophilic activity and consequently potential signaling capabilities. The methods used in this study detected six novel EFADs, as well as oxoETE (data not shown), that were produced by activated macrophages. To the best of our knowledge, five of these species have not been described before as relevant mediators of inflammation or as metabolic products formed by mammalian cells (EFAD-5 may correspond to oxoETrE). Interestingly, 15d-PGJ$_2$ was not observed in this study; the levels of 15d-PGJ$_2$ may have been too low for detection, implying that the novel species reported here may also be responsible for the effects often attributed to 15d-PGJ$_2$.

In taking the search for lipid mediators a step further, the Lipid Metabolites and Pathway Strategy consortium (Lipid MAPS; http://www.lipidmaps.org), has been publishing information focused on the lipid section of the metabolome and "global changes in lipid metabolites" (i.e. lipidomics) since 2005. While the methods used to date have identified new lipid metabolites and yielded valuable data on the signaling properties of these metabolites, they have their limitations and the potential to overlook lipids with unique or unconventional means of signal transduction. Other studies use methods that have focused exclusively on RES; by using MS/MS to detect and study RES-GSH adducts, it is possible to appreciate the in vivo signature left by various RES and to obtain structural information on RES of interest by using MS$^3$. However, there are also limitations in using this method. For example, RES generated in lipid bilayers may not have the opportunity to interact with GSH, but may still modify membrane associated proteins. This concept has already been used to characterize enzyme-generated RES produced by the hypersensitive response in tobacco leaves.

The inventors have developed an alternative to analyzing only RES-GSH adducts, in which an alkylation reaction of electrophiles to β-mercaptoethanol (BME) is used to identify electrophiles that can reversibly adduct to cellular sulfhydryls (or other nucleophiles). Conventionally, oxidized PUFA species have been discovered by hypothesizing the substrates, mechanisms/enzymes, and subsequently identifying the products of labeled substrates or identifying the hypothesized products, as compared to synthetic compounds. The success of this method is exemplified by the extensive knowledge of various PG species and the discovery of isoprostanes, neuroprostanes, lipoxins and Resolvins. Conversely, the oxidized lipid species reported in this study were initially discovered exclusively based on their chemical properties: negatively charged small hydrophobic molecules with reversible electrophilic activity. The BME method used herein increased MS/MS sensitivity for RES and standardized the behavior of a variety of RES during MS/MS analysis. For example, oxo-fatty acid derivatives do not fragment as well as the corresponding hydroxy-derivatives, rendering structural identification more difficult. Accordingly, one reason that the species described in this work have not been reported before may be that the typical method of lipid metabolite identification yields largely the expected or the most abundant species; unanticipated lipid species that might be produced and signal at lower concentrations would be relegated to the background of more prominent species in this method. In the present work we report previously uncharacterized electrophilic fatty acids, which were primarily derived by oxygenation of n-3 PUFAs. In particular, EFAD-1 to -3 corresponded to oxoDHA, oxoDPA and oxoDTA (with different isomers being formed depending on the presence of ASA). EFAD-4 to −6 were derived from n-6 and n-9 PUFAs. However, the low levels and the presence of several isomers did not allow a detailed structural characterization of these latter species.

Accordingly, the inducible enzyme COX-2 was required for EFADs biosynthesis although we cannot exclude the possibility that additional mechanisms may be involved in their formation. In fact, autoxidation of DHA to OH-DHA and the resulting formation of 10 positional isomers was reported early in the 1980s. LOXs (i.e. 5-LOX and in some cases 12-LOX and 15-LOX) can initiate the oxidation of PUFAs as well. Finally, cytochrome p450 (CYP) monooxygenases have been reported to catalyze the NADPH-dependent oxidation of PUFAs and CYP4F8 has been shown to catalyze the hydroxylation of AA and DPA (22:5n-6) mainly at the n-3 position. While the formation of hydroxy-derivatives of PUFAs has already been described, further oxidation to the corresponding oxo-species has only been observed for hydroxy-ETA. Moreover, despite the knowledge on (6E,8Z,11Z,14Z)-5-oxoicosa-6,8,11,14-tetranoic acid (5-oxoETE) and KODE, there is a lack of research on similar 22-carbon species. The oxidation of hydroxyl groups on bioactive lipids has been generally viewed as a step in metabolic inactivation, but we propose that such a reaction may instead confer novel beneficial biologic activity. Here we report a bifurcation at the point where hydroxy-derivatives of n-3 PUFAs could be further oxidized by LOXs to Rvs and neuroprotectins. We show that monohydroxy-PUFA derivatives are also converted to the corresponding carbonyl species generating bioactive electrophilic lipids.

Several dehydrogenase enzymes have already been described that could be involved in the second oxidation step of EFAD formation. For example, the enzyme 15-hydroxyprostaglandin dehydrogenase is a candidate for this reaction since it has been reported to catalyze the formation of 15-oxo-ETE and the oxidation of Resolvins D1 and E1 at position −17 Mol. Pharmacol. 2009 Jun. 17. [Epub ahead of print]). Similarly, the $LTB_4$ 12-hydroxy dehydrogenase/prostaglandin reductase ($LTB_4$12-HD/PGR) catalyzes the $NADP^+$-dependent reduction of hydroxy-eicosanoids to the corresponding α,β-unsaturated oxo-derivatives. In the case of 5-oxoETE formation, the 5-lipoxygenase product 5-hydroxyeicosatetranoic acid is further oxidized by 5-hydroxyeicosanoid dehydrogenase (5-HEDH) to 5-oxoETE. As HEDH can catalyze the reaction of 5-HETE to 5-oxoETE in both the forward and reverse direction, the formation of 5-oxoETE is favored by a high $NADP^+$:NADPH ratio (a condition symptomatic of cells under oxidative stress). It is interesting to note that while HEDH activity is present in myeloid cells, it is most significantly induced following differentiation to macrophages using PMA.

The adduction of EFADs to proteins and to GSH demonstrated the role they play as potential modulators of protein function and as electrophilic signal transducers. RES adduction to proteins, such as the covalent modification of GAPDH by $NO_2$-FA, can alter protein's activity or subcellular location. RES can also modulate gene expression by covalently binding to transcriptional regulators, as exemplified by $NO_2FA$ and 15d-$PGJ_2$ adduction to the p65 subunit of NFκB, thus preventing DNA binding. In other cases, RES form covalent adducts with proteins that associate with transcription factors (e.g. 15d-$PGJ_2$ adduction to the Nrf2 inhibitor Keap1). Moreover, RES participate in signaling by forming covalent adducts with GSH. Approximately 50% of the EFADs recovered from activated RAW264.7 cell lysate were adducted to protein (FIG. 9a), but this value did not include EFADs that were bound to small molecules such as GSH. Both intracellular and extracellular (secreted) GS-EFAD-2 (and GS-EFAD-1) adducts were identified by RP-HPLC-MS/MS. Interestingly, while both GS-13-oxoDPA and GS-17-oxoDPA adducts were detected intracellularly for RAW264.7 cells, only the GS-13-oxoDPA adduct was detected extracellularly. This observation may be due to several possibilities; treatment of RAW264.7 cells with ASA may affect the secretory pathway, GS-17-oxoDPA may not be secreted as efficiently as GS-13-oxoDPA, or GS-17-oxoDPA may be further metabolized more rapidly than GS-13-oxoDPA once secreted.

In addition to GSH and GAPDH-adduct formation, the modulation of several signaling pathways by EFADs confirmed their role as endogenously produced anti-inflammatory signaling mediators. According to their electrophilic nature, 17-oxoDHA and 17-oxoDPA induced the anti-oxidant response by promoting nuclear accumulation of Nrf2 and the expression of two major Nrf2 target genes, HO-1 and Nqo-1. The 17-oxo-standards also acted as agonists of PPARγ, suggesting that EFADs may exert some anti-inflammatory effects through PPARγ activation. This was consistent with previous observations that activation of PPARγ by low concentrations of the synthetic ligand Rosiglitazone inhibits the expression of a small set of IFNγ and LPS-dependent genes in primary mouse macrophages. Additionally, 17-oxoDPA and 17-oxoDHA inhibited IFNγ and LPS-induced cytokine production in a dose-dependent manner in RAW264.7 cells. Further evidence concerning the anti-inflammatory signaling properties of EFADs was the dose-dependent inhibition of iNOS expression and activity by 17-oxoDPA and 17-oxoDHA following macrophage activation with IFNγ and $Kdo_2$. Surprisingly, EFAD-1 and -2 did not affect NF-κB DNA binding activity, p65 nuclear translocation, or STAT-1 phosphorylation (data not shown) in RAW264.7 suggesting that the inhibition of cytokine and iNOS expression was independent of these signaling pathways. Interestingly, COX-2 induction in response to $Kdo_2$ and IFNγ was not affected by EFAD treatment. Overall these findings suggest that EFADs may exert their anti-inflammatory actions via pathways other than NF-κB and STAT-1. The activation of PPARγ may be a possibility especially because the activation of PPARγ differentially affects iNOS and COX-2 expression and can generate a pattern of cytokine expression similar to what we have observed without affecting NF-κB activation. Additional evidence supporting a role for EFADs as signaling mediators was the observation that 17-oxoDPA and 17-oxoDHA covalently bind Cys and His residues in GAPDH, giving a similar pattern to that previously observed for NO$_2$-FA. Finally, preliminary data indicate that EFAD-1 and 2—may promote cytoprotective effects via the activation of the heat shock response, possibly by inducing activation of the transcription factor Hsf1 and the subsequent transcription of target genes, such as Hsp70 and Hsp40. This would represent a further mechanism through which EFADs may exert their beneficial actions. Overall, while recognized signaling pathways that are modulated by electrophiles were tested, it is probable that EFADs each have their own unique signaling profiles and receptors. Further investigation is currently underway to elucidate these profiles.

The potential of the present discovery can be fully appreciated when considering EFADs biological properties as a whole: they are beneficial bioactive lipids derived from omega-3 fatty acids, produced via the action of COX-2 and whose formation is enhanced by aspirin. In this scenario, the yet-to-be fully elucidated beneficial roles of COX-2 and omega-3 fatty acids in resolution of inflammation and their crucial role in cardiovascular homeostasis suggest that COX-2 derived EFADs may contribute to mediating these actions. Furthermore, the ASA-dependent enhancement of EFAD biosynthesis further strengthens this hypothesis suggesting that the protective and anti-inflammatory effects of EFADs that we observed in cellular models may participate in transducing some of the beneficial actions of omega-3 fatty acids, COX-2 and ASA in human health.

CITATIONS

1. Connor, W. E. Importance of n-3 fatty acids in health and disease. *Am J Clin Nutr* 71, 171S-175S (2000).
2. Neuringer, M., Anderson, G. J. & Connor, W. E. The essentiality of n-3 fatty acids for the development and function of the retina and brain. *Annu Rev Nutr* 8, 517-541 (1988).
3. Morris, M. C., Evans, D. A., Tangney, C. C., Bienias, J. L. & Wilson, R. S. Fish consumption and cognitive decline with age in a large community study. *Arch Neurol* 62, 1849-1853 (2005).
4. Fedor, D. & Kelley, D. S. Prevention of insulin resistance by n-3 polyunsaturated fatty acids. *Curr Opin Clin Nutr Metab Care* 12, 138-146 (2009).
5. Dietary supplementation with n-3 polyunsaturated fatty acids and vitamin E after myocardial infarction: results of the GISSI-Prevenzione trial. Gruppo Italiano per lo Studio della Sopravvivenza nell'Infarto miocardico. *Lancet* 354, 447-455 (1999).
6. Duda, M. K., et al. Fish oil, but not flaxseed oil, decreases inflammation and prevents pressure overload-induced cardiac dysfunction. *Cardiovasc Res* 81, 319-327 (2009).
7. Harris, W. S., Assaad, B. & Poston, W. C. Tissue omega-6/omega-3 fatty acid ratio and risk for coronary artery disease. *Am J Cardiol* 98, 19i-26i (2006).
8. Arita, M., et al. Stereochemical assignment, antiinflammatory properties, and receptor for the omega-3 lipid mediator resolvin E1. *J Exp Med* 201, 713-722 (2005).
9. Kim, E. H. & Surh, Y. J. 15-deoxy-Delta12,14-prostaglandin J2 as a potential endogenous regulator of redox-sensitive transcription factors. *Biochem Pharmacol* 72, 1516-1528 (2006).
10. Serhan, C. N., Chiang, N. & Van Dyke, T. E. Resolving inflammation: dual anti-inflammatory and pro-resolution lipid mediators. *Nat Rev Immunol* 8, 349-361 (2008).
11. Cui, T., et al. Nitrated fatty acids: Endogenous anti-inflammatory signaling mediators. *J Biol Chem* 281, 35686-35698 (2006).
12. Musiek, E. S., et al. Electrophilic cyclopentenone neuroprostanes are anti-inflammatory mediators formed from the peroxidation of the omega-3 polyunsaturated fatty acid docosahexaenoic acid. *J Biol Chem* 283, 19927-19935 (2008).
13. Talalay, P., De Long, M. J. & Prochaska, H. J. Identification of a common chemical signal regulating the induction of enzymes that protect against chemical carcinogenesis. *Proc Natl Acad Sci USA* 85, 8261-8265 (1988).
14. Lin, D., Saleh, S. & Liebler, D. C. Reversibility of covalent electrophile-protein adducts and chemical toxicity. *Chem Res Toxicol* 21, 2361-2369 (2008).
15. Batthyany, C., et al. Reversible post-translational modification of proteins by nitrated fatty acids in vivo. *J Biol Chem* 281, 20450-20463 (2006).
16. Farmer, E. E. & Davoine, C. Reactive electrophile species. *Current Opinion in Plant Biology* 10, 380-386 (2007).
17. Satoh, T., et al. Activation of the Keap1/Nrf2 pathway for neuroprotection by electrophillic phase II inducers. *Proceedings of the National Academy of Sciences of the United States of America* 103, 768-773 (2006).
18. Haridas, V., et al. Avicins: triterpenoid saponins from *Acacia victoriae* (Bentham) induce apoptosis by mitochondrial perturbation. *Proc Natl Acad Sci USA* 98, 5821-5826 (2001).
19. Dinkova-Kostova, A. T., Cory, A. H., Bozak, R. E., Hicks, R. J. & Cory, J. G. Bis(2-hydroxybenzylidene)acetone, a potent inducer of the phase 2 response, causes apoptosis in mouse leukemia cells through a p53-independent, caspase-mediated pathway. *Cancer Lett* 245, 341-349 (2007).
20. Thornalley, P. J. Isothiocyanates: mechanism of cancer chemopreventive action. *Anticancer Drugs* 13, 331-338 (2002).
21. Mochizuki, M., et al. Role of 15-deoxy delta(12,14) prostaglandin J2 and Nrf2 pathways in protection against acute lung injury. *Am J Respir Crit Care Med* 171, 1260-1266 (2005).
22. Schopfer, F. J., et al. Detection and quantification of protein adduction by electrophilic fatty acids: mitochondrial generation of fatty acid nitroalkene derivatives. *Free Radic Biol Med* 46, 1250-1259 (2009).
23. Jean-Louis Luche, L. R.-H. a. P. C. Reduction of natural enones in the presence of cerium trichloride. *J. Chem. Soc., Chem. Commun.*, 601-602 (1978).
24. Gierse, J. K. a. K. C. M. Current Protocols in Pharmacology. in *Cyclooxygenase Assays* (ed. S. J., E.) (John Wiley and Sons, Inc., 1998).
25. Serhan, C. N., et al. Resolvins: a family of bioactive products of omega-3 fatty acid transformation circuits initiated by aspirin treatment that counter proinflammation signals. *J Exp Med* 196, 1025-1037 (2002).
26. Rouzer, C. A., et al. Lipid profiling reveals arachidonate deficiency in RAW264.7 cells: Structural and functional implications. *Biochemistry* 45, 14795-14808 (2006).
27. Ishikawa, T., Esterbauer, H. & Sies, H. Role of cardiac glutathione transferase and of the glutathione S-conjugate export system in biotransformation of 4-hydroxynonenal in the heart. *J Biol Chem* 261, 1576-1581 (1986).
28. Levonen, A.-L., et al. Cellular mechanisms of redox cell signalling: role of cysteine modification in controlling antioxidant defences in response to electrophilic lipid oxidation products. *Biochem J* 378, 373-382 (2004).
29. Murphy, R. C. & Zarini, S. Glutathione adducts of oxyeicosanoids. *Prostaglandins Other Lipid Mediat* 68-69, 471-482 (2002).
30. Waku, T., Shiraki, T., Oyama, T. & Morikawa, K. Atomic structure of mutant PPARgamma LBD complexed with 15d-PGJ2: novel modulation mechanism of PPARgamma/ RXRalpha function by covalently bound ligands. *FEBS Lett* 583, 320-324 (2009).
31. Itoh, T., et al. Structural basis for the activation of PPARgamma by oxidized fatty acids. *Nat Struct Mol Biol*, 924-931 (2008).
32. Harkewicz, R., Fahy, E., Andreyev, A. & Dennis, E. A. Arachidonate-derived dihomoprostaglandin production observed in endotoxin-stimulated macrophage-like cells. *J Biol Chem* 282, 2899-2910 (2007).
33. Davoine, C., Douki, T., Iacazio, G., Montillet, J. L. & Triantaphylides, C. Conjugation of keto fatty acids to glutathione in plant tissues. Characterization and quantification by HPLC-tandem mass spectrometry. *Anal Chem* 77, 7366-7372 (2005).
34. Davoine, C., et al. Adducts of oxylipin electrophiles to glutathione reflect a 13 specificity of the downstream lipoxygenase pathway in the tobacco hypersensitive response. *Plant Physiology* 140, 1484-1493 (2006).
35. Serhan, C. N., et al. Novel functional sets of lipid-derived mediators with antiinflammatory actions generated from omega-3 fatty acids via cyclooxygenase 2-nonsteroidal antiinflammatory drugs and transcellular processing. *J Exp Med* 192, 1197-1204 (2000).
36. VanRollins, M. & Murphy, R. C. Autooxidation of docosahexaenoic acid: analysis of ten isomers of hydroxy-docosahexaenoate. *J Lipid Res* 25, 507-517 (1984).
37. Stark, K., Wongsud, B., Burman, R. & Oliw, E. H. Oxygenation of polyunsaturated long chain fatty acids by recombinant CYP4F8 and CYP4F12 and catalytic importance of Tyr-125 and Gly-328 of CYP4F8. *Arch Biochem Biophys* 441, 174-181 (2005).
38. Schwartzman, M. L., Falck, J. R., Yadagiri, P. & Escalante, B. Metabolism of 20-hydroxyeicosatetraenoic acid by cyclooxygenase. Formation and identification of novel endothelium-dependent vasoconstrictor metabolites. *J Biol Chem* 264, 11658-11662 (1989).
39. Erlemann, K. R., et al. Regulation of 5-hydroxyeicosanoid dehydrogenase activity in monocytic cells. *Biochem J* 403, 157-165 (2007).
40. Arita, M., et al. Metabolic inactivation of resolvin E1 and stabilization of its anti-inflammatory actions. *J Biol Chem* 281, 22847-22854 (2006).
41. Sun, Y. P., et al. Resolvin D1 and its aspirin-triggered 17R epimer. Stereochemical assignments, anti-inflammatory properties, and enzymatic inactivation. *J Biol Chem* 282, 9323-9334 (2007).
42. Dick, R. A., Kwak, M. K., Sutter, T. R. & Kensler, T. W. Antioxidative function and substrate specificity of NAD(P)H-dependent alkenal/one oxidoreductase. A new role for leukotriene B4 12-hydroxydehydrogenase/15-oxoprostaglandin 13-reductase. *J Biol Chem* 276, 40803-40810 (2001).
43. Bowers, R. C., Hevko, J., Henson, P. M. & Murphy, R. C. A novel glutathione containing eicosanoid (FOG7) chemotactic for human granulocytes. *J Biol Chem* 275, 29931-29934 (2000).
44. Welch, J. S., Ricote, M., Akiyama, T. E., Gonzalez, F. J. & Glass, C. K. PPARgamma and PPARdelta negatively regulate specific subsets of lipopolysaccharide and IFN-gamma target genes in macrophages. *Proc Natl Acad Sci USA* 100, 6712-6717 (2003).
45. Jacobs, A. T. & Marnett, L. J. Heat shock factor 1 attenuates 4-Hydroxynonenal-mediated apoptosis: critical role for heat shock protein 70 induction and stabilization of Bcl-XL. *J Biol Chem* 282, 33412-33420 (2007).
46. Zheng, Z., Kim, J. Y., Ma, H., Lee, J. E. & Yenari, M. A. Anti-inflammatory effects of the 70 kDa heat shock protein in experimental stroke. *J Cereb Blood Flow Metab* 28, 53-63 (2008).
47. Alvarez, M. N., Trujillo, M. & Radi, R. Peroxynitrite formation from biochemical and cellular fluxes of nitric oxide and superoxide. *Methods in Enzymology* 359, 353-366 (2002).
48. Davies, J. Q. & Gordon, S. Isolation and culture of murine macrophages. *Methods Mol Biol* 290, 91-103 (2005).

What is claimed is:

1. A pharmaceutical formulation comprising: an effective amount of a compound having a formula of:

$$R_1 \underbrace{\phantom{xxx}}_{a} \overset{\overset{W}{\|}}{\underset{\underset{R_b}{|}}{V}} = \underset{\underset{c}{}}{\overset{R_b{}'}{\underset{|}{C}}} \underbrace{\phantom{xxx}}_{f}$$

wherein:
$R_1$ is a heterocyclyl;
===== is an optional double bond;
W is —OH, —C(O)H, —C(O), —C(O)$R^p$, —COOH, —COO$R^p$, —Cl, —Br, —I, —CF$_3$, —CN, —SO$_3$, —SO$_2R^p$, —SO$_3$H, —NH$_3^+$, —NH$_2R^{p+}$, —NR$^p$R$^q$R$^t$, —NO$_2$, =O, =NR$^p$, =CF$_2$, or =CHF;
each V is, independently —CH or —C—, wherein:
V is —CH— when W is —OH, —H, —C(O)H, —C(O), —C(O)$R^p$, —COON, —COO$R^p$, —Cl, —Br, —I, —F, —CF$_3$, —CN, —SO$_3$, —SO$_2R^p$, —SO$_3$H, —NH$^{3+}$, —NH$_2R^{p+}$, —NR$^p$R$^q$R$^t$ or —NO$_2$; or
V is —C— when W is =O, =NR$^p$, =CF$_2$ or =CHF;
$R^p$ and $R^q$ are each, independently, H, (C$_1$-C$_8$) alkyl, aryl, or (C$_1$-C$_8$) haloalkyl;
$R^t$ is (C$_1$-C$_8$) alkyl, aryl, or (C$_1$-C$_8$) haloalkyl;
$R^b$ and $R^{b'}$ are each independently, —H, —OH, —C(O)H, —C(O), —C(O)$R^p$, —COOH, —COO$R^p$, —Cl, —Br, —I, —F, —CF$_3$, —CHF$_2$, —CH$_2$F, —CN, —SO$_3$, —SO$_2R^p$, SO$_3$H, —NH$_3^+$, —NH$_2R^{p+}$, —NR$^p$R$^q$R$^t$ or —NO$_2$, wherein:
$R^b$ and $R^{b'}$ are not simultaneously non-hydrogen groups;
a is an integer between 5 and 15 inclusive, c is an integer from 1 and 15 inclusive, and f is an integer between 5 and 15 inclusive; and
a pharmaceutically acceptable carrier.

2. The formulation according to claim 1, wherein W is —H, =O or =NR$^p$.

3. The formulation according to claim 1, wherein V is —CH— and W is —H.

4. The formulation according to claim 1, wherein V is —C— and W is =O.

5. The formulation according to claim 1, wherein c is 1, V is —C—, and W is =O.

6. The formulation according to claim 1, wherein $R^b$ and $R^{b'}$, are each, independently, —H, —OH, —CN, or —NO$_2$.

7. The formulation according to claim 1, wherein $R^b$ and $R^{b'}$ are each —H.

8. The formulation according to claim 1, wherein a is 3.

9. The formulation according to claim 1, wherein the pharmaceutically acceptable carrier comprises a solid, solution, powder, fluid emulsion, fluid suspension, semi-solid, or dry powder.

10. The formulation according to claim 1, further comprising at least one pharmaceutically acceptable diluent, filler, disintegrant, binder, lubricant, surfactant, hydrophobic vehicle, water soluble vehicle, emulsifier, buffer, humectant, moisturizer, solubilizer, antioxidant, or preservative, or combinations thereof.

11. A compound having a formula of:

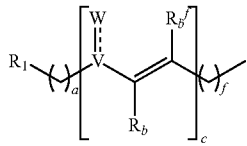

wherein:

$R_1$ is a heterocyclyl;

===== is an optional double bond;

W is —OH, —C(O)H, —C(O), —C(O)$R^p$, —COOH, —COO$R^p$, —Cl, —Br, —I, —CF$_3$, —CN, —SO$_3$, —SO$_2$$R^p$, —SO$_3$H, —NH$_3^+$, —NH$_2$$R^{p+}$, —N$R^p$$R^q$$R^t$, —NO$_2$, =O, =CF$_2$, or —CHF;

each V is, independently —CH or —C—, wherein:

V is —CH— when W is —OH, —H, —C(O)H, —C(O), —C(O)RP, —COOH, —COORP, —Cl, —Br, —I, —F, —CF$_3$, —CN, —SO$_3$, —SO$_2$RP, —SO$_3$H, —NH$^{3+}$, —NH$_2$RP$^+$, —N$R^p$$R^q$$R^t$ or —NO$_2$; or V is —C— when W is =O, =NRP, =CF$_2$ or =CHF;

$R^p$ and $R^q$ are each, independently, H, (C$_1$-C$_8$) alkyl, aryl, or (C$_1$-C$_8$) haloalkyl;

$R^t$ is (C$_1$-C$_8$) alkyl, aryl, or (C$_1$-C$_8$) haloalkyl;

$R^b$ and $R^{b'}$ are each independently, —H, —OH, —C(O)H, —C(O), —C(O)$R^p$, —COOH, —COO$R^p$, —Cl, —Br, —I, —F, —CF$_3$, —CHF$_2$, —CH$_2$F, —CN, —SO$_3$, —SO$_2$$R^p$, SO$_3$H, —NH$_3^+$, —NH$_2$$R^{p+}$, —N$R^p$$R^q$$R^t$ or NO$_2$, wherein:

$R^b$ and $R^{b'}$ are not simultaneously non-hydrogen groups;

a is an integer between 5 and 15 inclusive, c is an integer from 1 and 15 inclusive, and f is an integer between 5 and 15 inclusive.

12. The compound according to claim 11, wherein W is =O or =NRP.

13. The formulation of claim 1, wherein $R_1$ is a heteroaryl or a heterocycloalkyl.

14. The compound of claim 11, wherein $R_1$ is a heteroaryl or a heterocycloalkyl.

15. The compound according to claim 11, wherein V is —C— and W is =O.

16. The compound according to claim 15, wherein c is 1.

* * * * *